(12) United States Patent
Freeman et al.

(10) Patent No.: US 7,985,559 B2
(45) Date of Patent: Jul. 26, 2011

(54) METHODS OF SELECTING EPIDERMAL GROWTH FACTOR RECEPTOR (EGFR) BINDING AGENTS

(75) Inventors: Daniel J. Freeman, Newbury Park, CA (US); Jilin Sun, Thousand Oaks, CA (US); Kenneth H. Jung, Newbury Park, CA (US); Gary S. Elliott, Thousand Oaks, CA (US); Robert Radinsky, Thousand Oaks, CA (US)

(73) Assignee: AMGEN Inc., Thousand Oaks, CA (US)

( * ) Notice: Subject to any disclaimer, the term of this patent is extended or adjusted under 35 U.S.C. 154(b) by 0 days.

(21) Appl. No.: 12/288,341

(22) Filed: Oct. 17, 2008

(65) Prior Publication Data

US 2009/0123937 A1 May 14, 2009

Related U.S. Application Data

(60) Provisional application No. 60/999,602, filed on Oct. 19, 2007.

(51) Int. Cl.
*G01N 33/53* (2006.01)
*C07K 14/435* (2006.01)
(52) U.S. Cl. .......................................... 435/7.1; 530/350
(58) Field of Classification Search .................. None
See application file for complete search history.

(56) References Cited

FOREIGN PATENT DOCUMENTS
WO    WO 98/50433    11/1998

OTHER PUBLICATIONS

Amado et al., "Wild-type *KRAS* is required for panitumumab efficacy in patients with metastatic colorectal cancer," *J. Clin. Oncol*, 26:1626-1634 (2008).
Friedman et al., "Synergistic down-regulation of receptor tyrosine kinases by combinations of mAbs: Implications for cancer immunotherapy," *PNAS*, 102:1915-1920 (2005).
Imai et al., "Comparing antibody and small-molecule therapies for cancer," *Nature Reviews Cancer*, 6:714-727 (2006).
Johns et al., "Identification of the epitope for the epidermal growth factor receptor-specific monoclonal antibody 806 reveals that it preferentially recognizes an untethered form of the receptor," *J. Biol. Chem.*, 279: 30375-30384 (2004).
Li et al., "Structural basis for inhibition of the epidermal growth factor receptor by cetuximab," *Cancer Cell*, 7:301-311 (2005).
Ward et al., "The insulin and EGF receptor structures: new insights into ligand-induced receptor activation," *TRENDS in Biochemical Sciences*, 32: 129-137 (2007).
PCT Notification of Transmittal of the International Search Report and the Written Opinion of the International Searching Authority, or the Declaration, for International Application No. PCT/US2008/011882, dated Mar. 19, 2009.

*Primary Examiner* — Ruixiang Li
(74) *Attorney, Agent, or Firm* — Scott N. Bernstein

(57) ABSTRACT

The present application relates to methods of selecting EGFr binding agents. In certain embodiments, such EGFr binding agents bind to at least a portion of a panitumumab epitope on an EGFr. In certain embodiments, such EGFr binding agents do not bind to a panitumumab epitope on an EGFr.

13 Claims, 5 Drawing Sheets

Figure 1 human EGFr amino acid sequence (without 24 amino acid leader sequence):

```
   1                                   leekkv cggtsnkltq lgtfedhfls lqrmfnncev
  37 vlgnleityv qrnydlsflk tigevagyvl ialntverip lenlqiirgn myyensyala
  97 vlsnydankt glkelpmrnl qeilhgavrf snnpalcnve siqwrdivss dflsnmsmdf
 157 qnhlgscqkc dpscpngscw gageencqkl tkiicaqqcs grcrgkspsd cchnqcaagc
 217 tgpresdclv crkfrdeatc kdtcpplmly nptttyqmdvn pegkysfgat cvkkcprnyv
 277 vtdhgscvra cgadsyemee dgvrkckkce gpcrKVCNGI GIGEFKDSLS INATNIKHFK
 337 NCTSISGDLH ILPVAFRGDS FTHTPPLDPQ ELDILKTVKE ITGFLLIQAW PENRTDLHAF
 397 ENLEIIRGRT KQHGQFSLAV VSLNITSLGL RSLKEISDGD VIISGNKNLC YANTINWKKL
 457 FGTSGQKTKI ISNRGENSCK ATGQVCHALC SPEGCWGPEP RDCVScrnvs rgrecvdkcn
 517 llegeprefv enseciqchp eclpqamnit ctgrgpdnci qcahyidgph cvktcpagvm
 577 genntlvwky adaghvchlc hpnctygctg pglegcptng pkipsiatgm vgalllllvv
 637 algiglfmrr rhivrkrtlr rllqerelve pltpsgeapn qallrilket efkkikvlgs
 697 gafgtvykgl wipegekvki pvaikelrea tspkankeil deayvmasvd nphvcrllgi
 757 cltstvqlit qlmpfgclld yvrehkdnig sqyllnwcvq iakgmnyled rrlvhrdlaa
 817 rnvlvktpqh vkitdfglak llgaeekeyh aeggkvpikw malesilhri ythqsdvwsy
 877 gvtvwelmtf gskpydgipa seissilekg erlpqppict idvymimvkc wmidadsrpk
 937 freliiefsk mardpqrylv iqgdermhlp sptdsnfyra lmdeedmddv vdadeylipq
 997 qgffsspsts rtplsslsa tsnnstvaci drnglqscpi kedsflqrys sdptgalted
1057 siddtflpvp eyingsvpkr pagsvqnpvy hnqplnpaps rdphyqdphs tavgnpeyln
1117 tvqptcvnst fdspahwaqk gshqisldnp dyqqdffpke akpngifkgs taenaeylrv
1177 apqssefiga
              (SEQ ID NO: 1)
```

Figure 2B
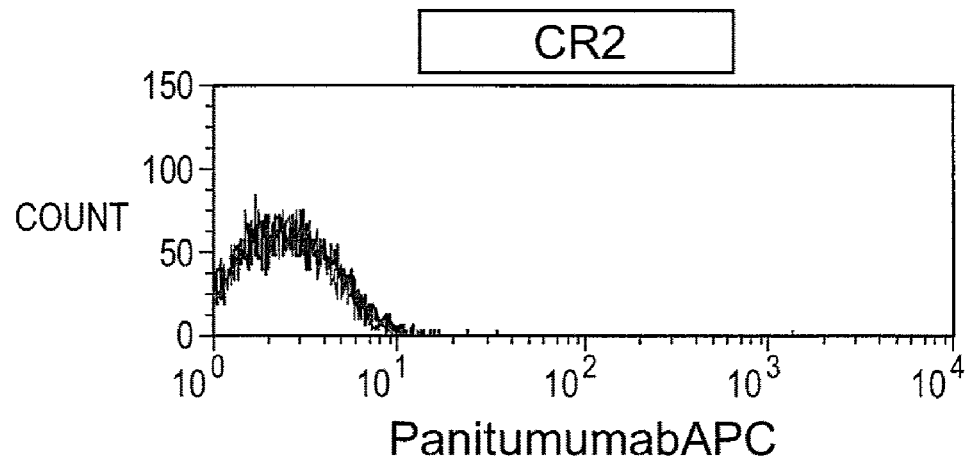
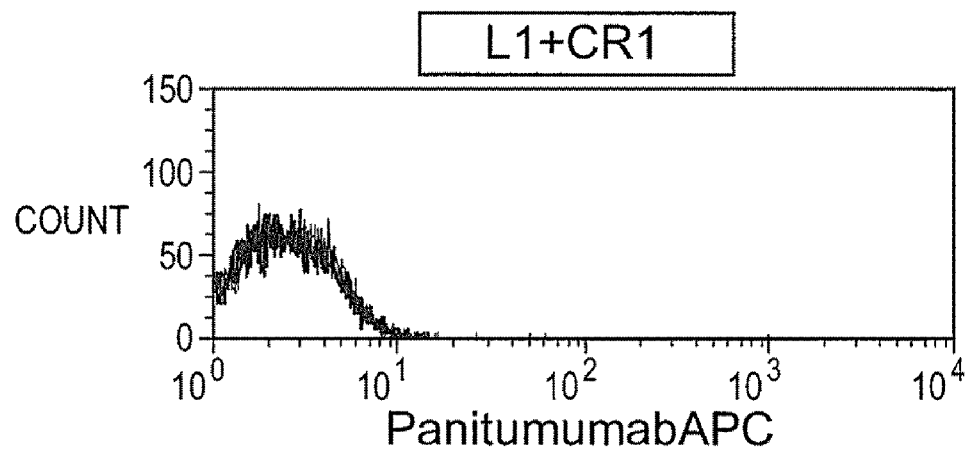
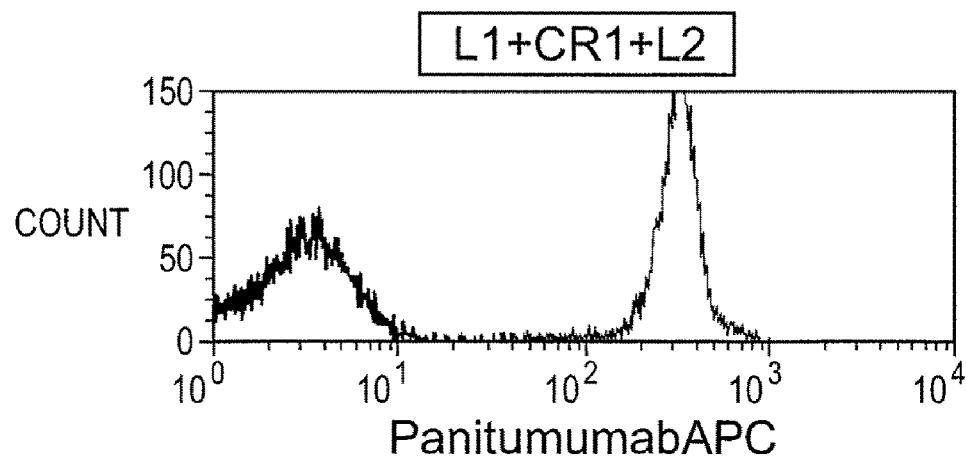

METHODS OF SELECTING EPIDERMAL GROWTH FACTOR RECEPTOR (EGFR) BINDING AGENTS

This application claims the benefit of U.S. Provisional Application No. 60/999,602, filed Oct. 19, 2007. U.S. Provisional Application No. 60/999,602 is incorporated herein by reference in its entirety for any purpose.

The present application relates to methods of selecting Epidermal Growth Factor Receptor (EGFr) binding agents. In certain embodiments, such EGFr binding agents bind to at least a portion of a panitumumab epitope on an EGFr. In certain embodiments, such EGFr binding agents do not bind to a panitumumab epitope on an EGFr.

BACKGROUND

Certain applications of monoclonal antibodies in cancer therapy use the ability of the antibody to specifically deliver to the cancerous tissues cytotoxic effector functions such as immune-enhancing isotypes, toxins or drugs. An alternative approach is to utilize monoclonal antibodies to directly affect the survival of tumor cells by depriving them of essential extracellular proliferation signals, such as those mediated by growth factors through their cell receptors. One of the attractive targets in this approach is the epidermal growth factor receptor (EGFr), which binds EGF and transforming growth factor α (TGFα) (see, e.g., Ullrich et al., Cell 61:203-212, 1990; Baselga et al., Pharmacol. Ther. 64:127-154, 1994; Mendelsohn et al., in Biologic Therapy of Cancer 607-623, Philadelphia:J. B. Lippincott Co., 1995; Fan et al., Curr. Opin. Oncol. 10:67-73, 1998). Binding of EGF or TGFα to EGFr, a 170 kDa transmembrane cell surface glycoprotein, triggers a cascade of cellular biochemical events, including EGFr autophosphorylation and internalization, which culminates in cell proliferation (see, e.g., Ullrich et al., Cell 61:203-212, 1990).

Several observations implicate EGFr in supporting development and progression of human solid tumors. EGFr has been demonstrated to be overexpressed on many types of human solid tumors (see, e.g., Mendelsohn *Cancer Cells* 7:359 (1989), Mendelsohn *Cancer Biology* 1:339-344 (1990), Modjtahedi and Dean *Int'l J. Oncology* 4:277-296 (1994)). For example, EGF-r overexpression has been observed in certain lung, breast, colon, gastric, brain, bladder, head and neck, ovarian, and prostate carcinomas (see, e.g., Modjtahedi and Dean *Int'l J. Oncology* 4:277-296 (1994)). The increase in receptor levels has been reported to be associated with a poor clinical prognosis (see, e.g., Baselga et al. *Pharmacol. Ther.* 64:127-154, 1994; Mendelsohn et al., *Biologic Therapy of Cancer* pp. 607-623, Philadelphia:J. B. Lippincott Co., 1995; Modjtahedi et al., *Intl. J. of Oncology* 4:277-296, 1994; Gullick, *Br. Medical Bulletin,* 47:87-98, 1991; Salomon et al., *Crit. Rev. Oncol. Hematol.* 19:183-232, 1995). Both epidermal growth factor (EGF) and transforming growth factor-alpha (TGF-α) have been demonstrated to bind to EGF-r and to lead to cellular proliferation and tumor growth. In many cases, increased surface EGFr expression was accompanied by production of TGFα or EGF by tumor cells, suggesting the involvement of an autocrine growth control in the progression of those tumors (see, e.g., Baselga et al. *Pharmacol. Ther.* 64:127-154, 1994; Mendelsohn et al., *Biologic Therapy of Cancer* pp. 607-623, Philadelphia:J. B. Lippincott Co., 1995; Modjtahedi et al., *Intl. J. of Oncology* 4:277-296, 1994; Salomon et al., *Crit. Rev. Oncol. Hematol.* 19:183-232, 1995).

Thus, certain groups have proposed that antibodies against EGF, TGF-α, and EGF-r may be useful in the therapy of tumors expressing or overexpressing EGF-r (see, e.g., Mendelsohn *Cancer Cells* 7:359 (1989), Mendelsohn *Cancer Biology* 1:339-344 (1990), Modjtahedi and Dean *Int'l J. Oncology* 4:277-296 (1994), Tosi et al. *Int'l J. Cancer* 62:643-650 (1995)). Indeed, it has been demonstrated that anti-EGF-r antibodies blocking EGF and TGF-α binding to the receptor appear to inhibit tumor cell proliferation. At the same time, however, anti-EGF-r antibodies have not appeared to inhibit EGF and TGF-α independent cell growth (Modjtahedi and Dean *Int'l J. Oncology* 4:277-296 (1994)).

Monoclonal antibodies specific to the human EGFr, capable of neutralizing EGF and TGFα binding to tumor cells and of inhibiting ligand-mediated cell proliferation in vitro, have been generated from mice and rats (see, e.g., Baselga et al., *Pharmacol. Ther.* 64:127-154, 1994; Mendelsohn et al., in *Biologic Therapy of Cancer* pp. 607-623, Philadelphia:J. B. Lippincott Co., 1995; Fan et al., *Curr. Opin. Oncol.* 10:67-73, 1998; Modjtahedi et al., *Intl. J. Oncology* 4:277-296, 1994). Some of those antibodies, such as the mouse 108, 225 (see, e.g., Aboud-Pirak et al., *J. Natl. Cancer Inst* 80:1605-1611, 1988) and 528 (see, e.g., Baselga et al., *Pharmacol. Ther.* 64:127-154, 1994; Mendelsohn et al., in *Biologic Therapy of Cancer* pp. 607-623, Philadelphia:J. B. Lippincott Co., 1995) or the rat ICR16, ICR62 and ICR64 (see, e.g., Modjtajedi et al., *Intl. J. Oncology* 4:277-296, 1994; Modjtahedi et al., *Br. J. Cancer* 67:247-253, 1993; Modjtahedi et al., *Br. J. Cancer* 67:254-261, 1993) monoclonal antibodies, were evaluated extensively for their ability to affect tumor growth in xenograft mouse models. Most of the anti-EGFr monoclonal antibodies were efficacious in preventing tumor formation in athymic mice when administered together with the human tumor cells (Baselga et al. *Pharmacol. Ther.* 64:127-154, 1994; Modjtahedi et al., *Br. J. Cancer* 67: 254-261, 1993). When injected into mice bearing established human tumor xenografts, the mouse monoclonal antibodies 225 and 528 caused partial tumor regression and required the co-administration of chemotherapeutic agents, such as doxorubicin or cisplatin, for eradication of the tumors (Baselga et al. *Pharmacol. Ther.* 64:127-154, 1994; Mendelsohn et al., in *Biologic Therapy of Cancer* pp. 607-623, Philadelphia:J. B. Lippincott Co., 1995; Fan et al., *Cancer Res.* 53:4637-4642, 1993; Baselga et al., *J. Natl. Cancer Inst.* 85: 1327-1333, 1993). A chimeric version of the 225 monoclonal antibody (C225), in which the mouse antibody variable regions are linked to human constant regions, exhibited an improved in vivo anti-tumor activity but only at high doses (see, e.g., Goldstein et al., *Clinical Cancer Res.* 1:1311-1318, 1995; Prewett et al., *J. Immunother. Emphasis Tumor Immunol.* 19:419-427, 1996). The rat ICR16, ICR62, and ICR64 antibodies caused regression of established tumors but not their complete eradication (Modjtahedi et al., *Br. J. Cancer* 67:254-261, 1993). These results established EGFr as a promising target for antibody therapy against EGFr-expressing solid tumors and led to human clinical trials with the C225 monoclonal antibody in multiple human solid cancers (see, e.g., Baselga et al. *Pharmacol. Ther.* 64:127-154, 1994; Mendelsohn et al., *Biologic Therapy of Cancer* pp. 607-623, Philadelphia:J. B. Lippincott Co., 1995; Modjtahedi et al., *Intl. J. of Oncology* 4:277-296, 1994).

Certain advances in the biological arts made it possible to produce a fully human anti-EGFr antibody. Using mice transgenic for human immunoglobulin genes (Xenomouse™ technology, Abgenix, Inc.), human antibodies specific for human EGFr were developed (see, e.g., Mendez, *Nature Genetics,* 15:146-156, 1997; Jakobovits, *Adv. Drug Deliv. Rev.,* 31 (1-2):33-42, 1998; Jakobovits, *Expert Opin. Invest. Drugs,* 7(4):607-614, 1998; Yang et al., *Crit. Rev. Oncol. Hematol.*

38(1):17-23, 2001; WO98/24893; WO 98/50433). One such antibody, panitumumab, a human IgG2 monoclonal antibody with an affinity of $5 \times 10^{-11}$ M for human EGFr, has been shown to block binding of EGF to the EGFr, to block receptor signaling, and to inhibit tumor cell activation and proliferation in vitro (see, e.g., WO98/50433; U.S. Pat. No. 6,235, 883). Studies in athymic mice have demonstrated that panitumumab also has in vivo activity, not only preventing the formation of human epidermoid carcinoma A431 xenografts in athymic mice, but also eradicating already-established large A431 tumor xenografts (see, e.g., Yang et al., *Crit. Rev. Oncol. Hematol.* 38(1):17-23, 2001; Yang et al., *Cancer Res.* 59(6):1236-43, 1999). Panitumumab has been considered for the treatment of renal carcinoma, colorectal adenocarcinoma, prostate cancer, and non small cell squamous lung carcinoma, among other cancers (see, e.g., U.S. Patent Publication No. 2004/0033543) Panitumumab has been approved by the Food & Drug Administration to treat patients with metastatic colorectal cancer.

SUMMARY

In certain embodiments, methods of selecting a specific binding agent to an epidermal growth factor receptor (EGFr) polypeptide are provided. In certain embodiments, the method selects a specific binding agent that binds to at least a portion of a panitumumab epitope on an EGFr polypeptide. In certain embodiments, the method comprises a) contacting an EGFr polypeptide with an agent; b) determining the affinity of the agent for the EGFr polypeptide; c) contacting a mutant EGFr polypeptide with the agent, wherein the mutant EGFr polypeptide comprises at least one point mutation at at least one amino acid position selected from P349, D355, F412, I438, K443, K465, and I467; d) determining the affinity of the agent for the mutant EGFr polypeptide; and e) selecting the agent if the affinity for the EGFr polypeptide is greater than the affinity for the mutant EGFr polypeptide.

In certain embodiments, the method comprises a) contacting a first EGFr polypeptide with an agent, wherein the first EGFr polypeptide comprises an L2 domain; b) determining the affinity of the agent for the first EGFr polypeptide; c) contacting a second EGFr polypeptide with the agent, wherein the second EGFr polypeptide lacks an L2 domain; d) determining the affinity of the agent for the second EGFr polypeptide; and e) selecting the agent if the affinity for the first EGFr polypeptide is greater than the affinity for the second EGFr polypeptide.

In certain embodiments, methods of selecting a specific binding agent to an epidermal growth factor receptor (EGFr) polypeptide are provided. In certain embodiments, the method selects a specific binding agent does not bind to a panitumumab epitope on an EGFr polypeptide (EGFr). In certain embodiments, the method comprises a) contacting an EGFr polypeptide with an agent; b) determining the affinity of the agent for the EGFr polypeptide; c) contacting a mutant EGFr polypeptide with the agent, wherein the mutant EGFr polypeptide comprises at least one point mutation at least one amino acid position selected from P349, D355, F412, I438, K443, K465, and I467; d) determining the affinity of the agent for the mutant EGFr polypeptide; and e) selecting the agent if the affinity for the EGFr polypeptide is similar to the affinity for the mutant EGFr polypeptide.

In certain embodiments, the method comprises a) contacting a first EGFr polypeptide with an agent, wherein the first EGFr polypeptide comprises an L2 domain; b) determining the affinity of the agent for the first EGFr polypeptide; c) contacting a second EGFr polypeptide with the agent, wherein the second EGFr polypeptide lacks an L2 domain; d) determining the affinity of the agent for the second EGFr polypeptide; and e) selecting the agent if the affinity for the first EGFr polypeptide is similar to the affinity for the second EGFr polypeptide.

BRIEF DESCRIPTION OF THE FIGURES

FIG. 1 shows the amino acid sequence of human EGFr (SEQ ID NO: 1). The L1, CR1, L2, CR2, and transmembrane domains are indicated on the figure. The amino acid residues P349, D355, F412, I438, K443, K465, and I467 are also indicated on the figure.

FIGS. 2A and 2B show binding of panitumumab to certain EGFr protein fragments, as described in Example 1.

DETAILED DESCRIPTION OF CERTAIN EMBODIMENTS

Figure 2A:
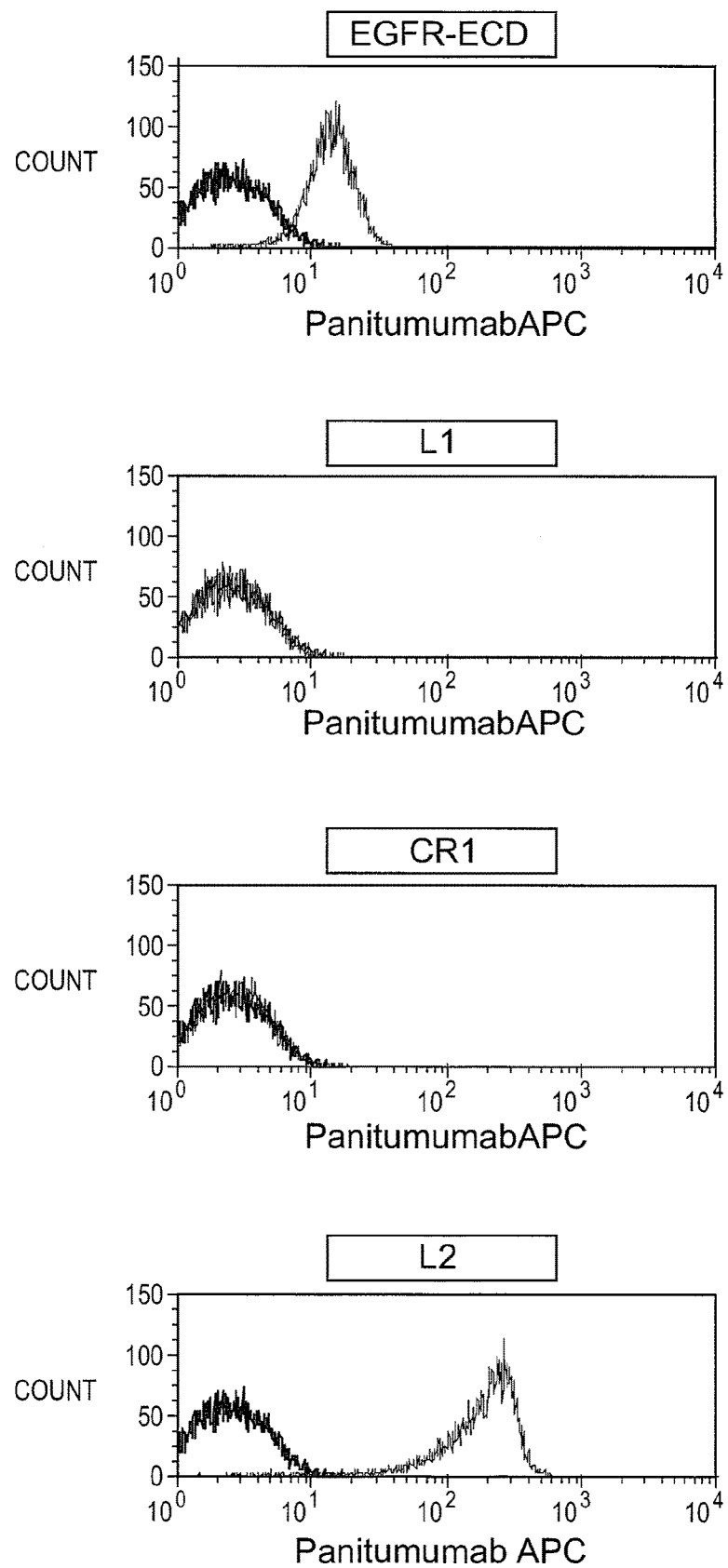

The section headings used herein are for organizational purposes only and are not to be construed as limiting the subject matter described. All documents or portions of documents cited in this application, including but not limited to patents, patent applications, articles, books, and treatises, are expressly incorporated by reference herein in their entirety for any purpose. In the event that one or more of the documents, or portions of documents, incorporated by reference defines a term that contradicts that term's definition in this application, this application controls.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, delivery, and treatment of patients.

In this application, the use of the singular includes the plural unless specifically stated otherwise. In this application, the word "a" or "an" means "at least one" unless specifically stated otherwise. In this application, the use of "or" means "and/or" unless specifically stated otherwise. In the context of a multiple dependent claim, the use of "or" refers back to more than one preceding independent or dependent claim in the alternative only. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

DEFINITIONS

Unless otherwise defined, scientific and technical terms used in connection with the present invention shall have the meanings that are commonly understood by those of ordinary skill in the art. As utilized in accordance with the present disclosure, the following terms, unless otherwise indicated, shall be understood to have the following meanings:

The terms "isolated polynucleotide" and "isolated nucleic acid" are used interchangeably, and refer to a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The terms "isolated protein" and "isolated polypeptide" and "isolated peptide" are used interchangeably, and refer to any polypeptide that (1) is free of at least some proteins with which it would normally be found, (2) is essentially free of other proteins from the same source, e.g., from the same species, (3) is expressed by a cell from a different species, or (4) does not occur in nature.

The terms "polypeptide" and "protein" are used interchangeably and are used herein as a generic term to refer to native protein, fragments, peptides, or analogs of a polypeptide sequence. Hence, native protein, fragments, and analogs are species of the polypeptide genus.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "D355T" with reference to the EGFr polypeptide indicates that there is an aspartic acid at amino acid number 355 of the wild-type EGFr sequence, and that aspartic acid is replaced with a threonine in the mutant EGFr sequence.

The terms "EGFr polypeptide" and "EGFr protein" are used interchangeably, and refer to a human EGFr polypeptide or fragment thereof, wherein the fragment thereof comprises at least one domain selected from an L1 domain, a CR1 domain, an L2 domain, and a CR2 domain. The amino acid sequence of an exemplary human EGFr polypeptide, without the 24 amino acid leader sequence, is shown in SEQ ID NO: 1 and in FIG. 1. In certain embodiments, an EGFr polypeptide comprises an L2 domain. In certain embodiments, an EGFr polypeptide lacks an L2 domain. An EGFr extracellular domain ("ECD") polypeptide is an EGFr polypeptide that lacks the cytoplasmic and transmembrane domains. The amino acid sequence of an exemplary human EGFr ECD is shown in SEQ ID NO: 2. In certain embodiments, an EGFr ECD polypeptide comprises an L1 domain, a CR1 domain, an L2 domain, and a CR2 domain. In certain embodiments, an EGFr ECD polypeptide comprises an L2 domain. In certain embodiments, an EGFr ECD polypeptide lacks an L2 domain. The amino acid sequences for an exemplary L1 domain, an exemplary CR1 domain, an exemplary L2 domain, and an exemplary CR2 domain are shown in SEQ ID NOs:4, 5, 3, and 6, respectively. In certain instances, epidermal growth factor (EGF) binds to the L2 domain of an EGFr polypeptide.

A "binding fragment" of an EGFr polypeptide, as used herein, refers to a fragment of an EGFr polypeptide that is capable of binding to panitumumab. In certain embodiments, a binding fragment comprises the extracellular domain ("ECD") of EGFr. In certain embodiments, a binding fragment comprises the L2 domain of EGFr. In certain embodiments, a binding fragment comprises the amino acid sequence of SEQ ID NO: 3.

The terms "mutant EGFr polypeptide" and "mutant EGFr protein" are used interchangeably, and refer to a human EGFr polypeptide comprising at least one point mutation in the extracellular domain. In certain embodiments, a mutant EGFr polypeptide comprises at least one point mutation at least one amino acid position selected from P349, D355, F412, I438, K443, K465, and I467. In certain embodiments, a mutant EGFr polypeptide comprises at least one point mutation selected from P349A, D355T, F412A, I438A, K443A, K465A, and I467A.

A mutant EGFr extracellular domain ("ECD") polypeptide is a mutant EGFr polypeptide that lacks the cytoplasmic and transmembrane domains. In certain embodiments, a mutant EGFr ECD polypeptide comprises at least one point mutation at least one amino acid position selected from P349, D355, F412, I438, K443, K465, and I467. In certain embodiments, a mutant EGFr ECD polypeptide comprises at least one point mutation selected from P349A, D355T, F412A, I438A, K443A, K465A, and I467A.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" refers to components that are in a relationship permitting them to function in their intended manner. For example, in the context of a polynucleotide sequence, a control sequence may be "operably linked" to a coding sequence when the control sequence and coding sequence are in association with each other in such a way that expression of the coding sequence is achieved under conditions compatible with the functioning of the control sequence.

The term "control sequence" refers to polynucleotide sequences which may effect the expression and processing of coding sequences with which they are in association. The nature of such control sequences may differ depending upon the host organism. Certain exemplary control sequences for prokaryotes include, but are not limited to, promoters, ribosomal binding sites, and transcription termination sequences. Certain exemplary control sequences for eukaryotes include, but are not limited to, promoters, enhancers, and transcription termination sequences. In certain embodiments, "control sequences" can include leader sequences and/or fusion partner sequences.

The terms "polynucleotide" and "oligonucleotide" are used interchangeably, and as referred to herein means a polymeric form of nucleotides of at least 10 bases in length. In certain embodiments, the bases may comprise at least one of ribonucleotides, deoxyribonucleotides, and a modified form of either type of nucleotide. The term includes single and double stranded forms of DNA.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction. Sequence regions on the DNA strand having the same sequence as the RNA and which are 5' to the 5' end of the RNA transcript are referred to as "upstream sequences". Sequence regions on the DNA strand having the same sequence as the RNA and which are 3' to the 3' end of the RNA transcript are referred to as "downstream sequences".

The terms "mutant EGFr polynucleotide", "mutant EGFr oligonucleotide," and "mutant EGFr nucleic acid" are used interchangeably, and refer to a polynucleotide encoding a mutant EGFr polypeptide.

The terms "mutant EGFr ECD polynucleotide", "mutant EGFr ECD oligonucleotide," and "mutant EGFr ECD nucleic acid" are used interchangeably, and refer to a polynucleotide encoding a mutant EGFr ECD polypeptide.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. The term "amino acid" or "amino acid residue," as used herein, refers to naturally occurring L amino acids or to D amino acids. The commonly used one- and three-letter abbreviations for amino acids are used herein (Bruce Alberts et al., *Molecular Biology of the Cell*, Garland Publishing, Inc., New York (4th ed. 2002)). Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include, but are not limited to:4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

In certain embodiments, conservative amino acid substitutions include substitution with one or more unconventional amino acid residues. In certain embodiments, unconventional amino acid residues are incorporated by chemical peptide synthesis rather than by synthesis in biological systems.

The term "acidic residue" refers to an amino acid residue in D- or L-form that comprises at least one acidic group when incorporated into a polypeptide between two other amino acid residues that are the same or different. In certain embodiments, an acidic residue comprises a sidechain that comprises at least one acidic group. Exemplary acidic residues include, but are not limited to, aspartic acid (D) and glutamic acid (E). In certain embodiments, an acidic residue may be an unconventional amino acid.

The term "aromatic residue" refers to an amino acid residue in D- or L-form that comprises at least one aromatic group. In certain embodiments, an aromatic residue comprises a sidechain that comprises at least one aromatic group. Exemplary aromatic residues include, but are not limited to, phenylalanine (F), tyrosine (Y), and tryptophan (W). In certain embodiments, an aromatic residue may be an unconventional amino acid.

The term "basic residue" refers to an amino acid residue in F- or L-form that may comprise at least one basic group when incorporated into a polypeptide next to one or more amino acid residues that are the same or different. In certain embodiments, a basic residue comprises a sidechain that comprises at least one basic group. Exemplary basic residues include, but are not limited to, histidine (H), lysine (K), and arginine (R). In certain embodiments, a basic residue may be an unconventional amino acid.

The term "neutral hydrophilic residue" refers to an amino acid residue in D- or L-form that comprises at least one hydrophilic and/or polar group, but does not comprise an acidic or basic group when incorporated into a polypeptide next to one or more amino acid residues that are the same or different. Exemplary neutral hydrophilic residues include, but are not limited to, alanine (A), cysteine (C), serine (S), threonine (T), asparagine (N), and glutamine (Q). In certain embodiments, a neutral hydrophilic residue may be an unconventional amino acid.

The terms "lipophilic residue" and "Laa" refer to an amino acid residue in D- or L-form having at least one uncharged, aliphatic and/or aromatic group. In certain embodiments, a lipophilic residue comprises a side chain that comprises at least one uncharged, aliphatic, and/or aromatic group. Exemplary lipophilic sidechains include, but are not limited to, alanine (A), phenylalanine (F), isoleucine (I), leucine (L), norleucine (Nle), methionine (M), valine (V), tryptophan (W), and tyrosine (Y). In certain embodiments, a lipophilic residue may be an unconventional amino acid.

The term "amphiphilic residue" refers to an amino acid residue in D- or L-form that is capable of being either a hydrophilic or lipophilic residue. An exemplary amphiphilic residue includes, but is not limited to, alanine (A). In certain embodiments, an amphiphilic residue may be an unconventional amino acid.

The term "nonfunctional residue" refers to an amino acid residue in D- or L-form that lacks acidic, basic, and aromatic groups when incorporated into a polypeptide next to one or more amino acid residues that are the same or different. Exemplary nonfunctional amino acid residues include, but are not limited to, methionine (M), glycine (G), alanine (A), valine (V), isoleucine (I), leucine (L), and norleucine (Nle). In certain embodiments, a nonfunctional residue may be an unconventional amino acid.

In certain embodiments, glycine (G) and proline (P) are considered amino acid residues that can influence polypeptide chain orientation.

In certain embodiments, a conservative substitution may involve replacing a member of one residue type with a member of the same residue type. As a non-limiting example, in certain embodiments, a conservative substitution may involve replacing an acidic residue, such as D, with a different acidic residue, such as E. In certain embodiments, a non-conservative substitution may involve replacing a member of one residue type with a member of a different residue type. As a non-limiting example, in certain embodiments, a non-conservative substitution may involve replacing an acidic residue, such as D, with a basic residue, such as K. In certain embodiments, a cysteine residue is substituted with another amino acid residue to prevent disulfide bond formation with that position in the polypeptide.

In making conservative or non-conservative substitutions, according to certain embodiments, the hydropathic index of amino acids may be considered. Each amino acid has been assigned a hydropathic index on the basis of its hydrophobicity and charge characteristics. The hydropathic indices of the 20 naturally-occurring amino acids are:isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known in certain instances that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made, effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the polypeptide.

The following hydrophilicity values have been assigned to these amino acid residues:arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. In certain instances, one may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | More specific exemplary Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In certain embodiments, conservative amino acid substitutions encompass non-naturally occurring amino acid residues, which are typically incorporated by chemical peptide synthesis rather than by synthesis in biological systems. Those non-naturally occurring amino acid residues include, but are not limited to, peptidomimetics and other reversed or inverted forms of amino acid moieties.

A skilled artisan will be able to determine suitable substitution variants of a reference polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity, including, but not limited to, the CDRs of an antibody, or that may be important for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity and/or structure. In view of such a comparison, in certain embodiments, one can predict the importance of amino acid residues in a polypeptide that correspond to amino acid residues which are important for activity or structure in similar polypeptides. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. For example, in certain embodiments, the variants can be screened for their ability to bind to CD40L. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided, either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested that there are a limited number of foldsin a given polypeptide or protein and that once a critical number of structures have been resolved, structural prediction will become dramatically more accurate. See, e.g., Brenner et al., *Curr. Op. Struct. Biol.*, 7(3):369-376 (1997).

Additional exemplary methods of predicting secondary structure include, but are not limited to, "threading" (Jones, D., *Curr. Opin. Struct. Biol.*, 7(3):377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Holm, supra (1999), and Brenner, supra (1997).).

In certain embodiments, the identity and similarity of related polypeptides can be readily calculated by known methods. Such methods include, but are not limited to, those described in Computational Molecular Biology, Lesk, A. M., ed., Oxford University Press, New York (1988); Biocomputing:Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988). In certain embodiments, polypeptides have amino acid sequences that are about 90 percent, or about 95 percent, or about 96 percent, or about 97 percent, or about 98 percent, or about 99 percent identical to amino acid sequences shown in FIGS. 1-74.

In certain embodiments, methods to determine identity are designed to give the largest match between the sequences tested. In certain embodiments, certain methods to determine identity are described in publicly available computer programs. Certain computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). In certain embodiments, the Smith Waterman algorithm, which is known in the art, may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix is also used by the algorithm. See, e.g., Dayhoff et al., *Atlas of Protein Sequence and Structure*, 5(3)(1978) for the PAM 250 comparison matrix; Henikoff et al., *Proc. Natl. Acad. Sci* USA, 89:10915-10919 (1992) for the BLOSUM 62 comparison matrix.

In certain embodiments, the parameters for a polypeptide sequence comparison include the following:

Algorithm: Needleman et al., J. Mol. Biol., 48: 443-453 (1970);
Comparison matrix: BLOSUM 62 from Henikoff et al., supra (1992);
Gap Penalty: 12
Gap Length Penalty: 4
Threshold of Similarity: 0

In certain embodiments, the GAP program may be useful with the above parameters. In certain embodiments, the aforementioned parameters are the default parameters for polypeptide comparisons (along with no penalty for end gaps) using the GAP algorithm.

According to certain embodiments, amino acid substitutions are those which:(1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts).

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger TINS p. 392 (1985); and Evans et al. *J. Med. Chem.* 30:1229 (1987). Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from:—$CH_2NH$—, —$CH_2S$—, —$CH_2$—$CH_2$—, —$CH$=$CH$— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992)); for example, by adding internal cysteine residues capable of forming intramolecular disulfide bridges which cyclize the peptide.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an antibody. In certain embodiments, a specific binding agent is an antigen binding region.

The term "specific binding agent to an EGFr polypeptide" refers to a specific binding agent that specifically binds any portion of an EGFr polypeptide. In certain embodiments, a specific binding agent to an EGFr polypeptide is an antibody to an EGFr polypeptide. In certain embodiments, a specific binding agent to an EGFr polypeptide is an antigen binding region. In certain embodiments, a specific binding agent to an EGFr polypeptide is an antibody to EGFr. In certain embodiments, a specific binding agent to an EGFr polypeptide is panitumumab.

The term "specifically binds" refers to the ability of a specific binding agent to bind to a target with greater affinity than it binds to a non-target. In certain embodiments, specific binding refers to binding for a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore® assay. In certain embodiments, affinity is determined by a kinetic method. In certain embodiments, affinity is determined by an equilibrium/solution method. In certain embodiments, affinity is determined using flow cytometry.

The affinity of an agent for a first polypeptide is "similar" to the affinity of the agent for a second polypeptide when there is less than a 2-fold difference in the affinities as determined by a selected method. The affinity of an agent for a first polypeptide is "greater" than the affinity of the agent for a second polypeptide when the affinity of the agent for the first polypeptide is at least 2-fold greater than the affinity for the agent for the second polypeptide as determined by a selected method.

"Native antibodies" and "native immunoglobulins", in certain instances, are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985; Novotny and Haber, *Proc. Natl. Acad. Sci. U.S.A.* 82:4592 (1985); Chothia et al., *Nature* 342:877-883 (1989)).

"Antibody" or "antibody peptide(s)" both refer to an intact antibody, or a fragment thereof. In certain embodiments, the fragment includes contiguous portions of an intact antibody. In certain embodiments, the fragment includes non-contiguous portions of an intact antibody. In certain embodiments, the antibody fragment may be a binding fragment that competes with the intact antibody for specific binding. The term "antibody" also encompasses polyclonal antibodies and monoclonal antibodies. In certain embodiments, binding fragments are produced by recombinant DNA techniques. In certain embodiments, binding fragments are produced by enzymatic or chemical cleavage of intact antibodies. Binding fragments include, but are not limited to, Fab, Fab', F(ab')2, Fv, scFv, maxibodies, and single-chain antibodies. Non-antigen binding fragments include, but are not limited to, Fc fragments. The term "antibody" also encompasses anti-idiotypic antibodies that specifically bind to the variable region of another antibody. In certain embodiments, an anti-idiotypic antibody specifically binds to the variable region of an anti-EGFr antibody. In certain embodiments, anti-idiotypic antibodies may be used to detect the presence of a particular anti-EGFr antibody in a sample or to block the activity of an anti-EGFr antibody.

The term "polyclonal antibody" refers to a heterogeneous mixture of antibodies that bind to different epitopes of the same antigen.

The term "monoclonal antibodies" refers to a collection of antibodies encoded by the same nucleic acid molecule. In certain embodiments, monoclonal antibodies are produced by a single hybridoma or other cell line, or by a transgenic mammal. Monoclonal antibodies typically recognize the same epitope. The term "monoclonal" is not limited to any particular method for making an antibody.

"Chimeric antibody" refers to an antibody that has an antibody variable region of a first species fused to another molecule, for example, an antibody constant region of another second species. See, e.g., U.S. Pat. No. 4,816,567 and Morrison et al., *Proc Natl Acad Sci* (USA), 81:6851-6855 (1985). In certain embodiments, the first species may be different from the second species. In certain embodiments, the first species may be the same as the second species. In certain embodiments, a chimeric antibody is a CDR-grafted antibody.

The term "CDR-grafted antibody" refers to an antibody in which the CDR from one antibody is inserted into the framework of another antibody. In certain embodiments, the antibody from which the CDR is derived and the antibody from which the framework is derived are of different species. In certain embodiments, the antibody from which the CDR is derived and the antibody from which the framework is derived are of different isotypes.

The term "multi-specific antibody" refers to an antibody wherein two or more variable regions bind to different epitopes. The epitopes may be on the same or different targets. In certain embodiments, a multi-specific antibody is a "bi-specific antibody," which recognizes two different epitopes on the same or different antigens.

The term "catalytic antibody" refers to an antibody in which one or more catalytic moieties is attached. In certain embodiments, a catalytic antibody is a cytotoxic antibody, which comprise a cytotoxic moiety.

The term "humanized antibody" refers to an antibody in which all or part of an antibody framework region is derived from a human, but all or part of one or more CDR regions is derived from another species, for example, including, but not limited to, a mouse.

The term "fully human antibody" refers to an antibody in which both the CDR and the framework comprise substantially human sequences. In certain embodiments, fully human antibodies are produced in non-human mammals, including, but not limited to, mice, rats, and lagomorphs. In certain embodiments, fully human antibodies are produced in hybridoma cells. In certain embodiments, fully human antibodies are produced recombinantly.

The term "anti-idiotype antibody" refers to an antibody that specifically binds to another antibody.

The term "heavy chain" includes any polypeptide having sufficient variable region sequence to confer specificity for a target. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxy-terminus. The term "heavy chain", as used herein, encompasses a full-length heavy chain and fragments thereof.

The term "light chain" includes any polypeptide having sufficient variable region sequence to confer specificity for a target. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof.

The term "Fab fragment" refers to an antibody comprising one light chain and the $C_H1$ and variable regions of one heavy chain. The heavy chain of a Fab fragment cannot form a disulfide bond with another heavy chain. In certain embodiments, the heavy chain of a Fab fragment forms a disulfide bond with the light chain of a Fab fragment.

The term "Fab' fragment" refers to an antibody comprising one light chain, the variable and $C_H1$ regions of one heavy chain, and some of the constant region between the $C_H1$ and $C_H2$ domains of the heavy chain. In certain embodiments, an interchain disulfide bond can be formed between two heavy chains of an Fab' fragment to form a $F(ab')_2$ molecule.

The term "$F(ab')_2$ molecule" refers to an antibody comprising two Fab' fragments connected by an interchain disulfide bond formed between two heavy chains.

An "Fv molecule" comprises the variable regions from both the heavy and light chains, but lacks the constant regions. A single chain variable fragment (scFv) comprises variable regions from both a heavy and a light chain wherein the heavy and light chain variable regions are fused to form a single polypeptide chain which forms an antigen-binding region. In certain embodiments, a scFV comprises a single polypeptide chain. A single-chain antibody comprises a scFV. In certain embodiments, a single-chain antibody comprises one or more additional polypeptides fused to a scFv. Exemplary additional polypeptides include, but are not limited to, one or more constant regions. Exemplary single-chain antibodies are discussed, e.g., in WO 88/01649 and U.S. Pat. Nos. 4,946,778 and 5,260,203.

The term "maxibody" refers to a scFv fused (may be by a linker or direct attachment) to an Fc or an Fc fragment. In certain embodiments, a single chain antibody is a maxibody. In certain embodiments, a single chain antibody is a maxibody that binds to EGFr. Exemplary Ig-like domain-Fc fusions are disclosed in U.S. Pat. No. 6,117,655.

An "Fc fragment" comprises the $C_H2$ and $C_H3$ domains of the heavy chain and contains some of the constant region, between the $C_H1$ and $C_H2$ domains, such that an interchain disulfide bond can be formed between two heavy chains.

As used herein, a "flexible linker" refers to any linker that is not predicted by one skilled in the art, according to its chemical structure, to be fixed in three-dimensional space. In certain embodiments, a peptide linker comprising three or more amino acids is a flexible linker.

The terms "variable region" and "variable domain" are used interchangeably herein to refer to a portion of the light and/or heavy chains of an antibody. In various instances, variable domains include approximately the amino-terminal 120 to 130 amino acids in the heavy chain and about 100 to 110 amino-terminal amino acids in the light chain. In certain embodiments, variable regions of different antibodies differ extensively in amino acid sequence even among antibodies of the same species. The variable region of an antibody, in various instances, determines specificity of a particular antibody for its target.

The term "immunologically functional immunoglobulin fragment" refers to a polypeptide fragment comprising at least the variable domains of an immunoglobulin heavy chain and an immunoglobulin light chain. In certain embodiments, an immunologically functional immunoglobulin fragment is capable of binding to a ligand, preventing binding of the ligand to its receptor, and thereby interrupting a biological response resulting from ligand binding to the receptor. In certain embodiments, an immunologically functional immunoglobulin fragment is capable of binding to a receptor, preventing binding of the ligand to its receptor, and thereby interrupting a biological response resulting from ligand binding to the receptor. In certain embodiments, an immunologically functional immunoglobulin fragment is capable of binding a receptor and activating that receptor. In certain embodiments, an immunologically functional immunoglobulin fragment is capable of binding a receptor and inactivating that receptor.

The term "epitope" refers to a portion of a molecule capable, of being bound by a specific binding agent. Exemplary epitopes may comprise any polypeptide determinant capable of specific binding to an immunoglobulin and/or T-cell receptor. Exemplary epitope determinants include, but are not limited to, chemically active surface groupings of molecules, for example, but not limited to, amino acids, sugar side chains, phosphoryl groups, and sulfonyl groups. In certain embodiments, epitope determinants may have specific three dimensional structural characteristics, and/or specific charge characteristics. In certain embodiments, an epitope is a region of an antigen that is bound by an antibody. Epitopes may be contiguous or non-contiguous. In certain embodiments, epitopes may be mimetic in that they comprise a three dimensional structure that is similar to an epitope used to generate the antibody, yet comprise none or only some of the amino acid residues found in that epitope used to generate the antibody.

The term "panitumumab epitope" refers to an epitope on an EGFr polypeptide that is specifically bound by panitumumab. In certain embodiments, a panitumumab epitope comprises at least a portion of the L2 domain of EGFr. In certain embodiments, a panitumumab epitope comprises at least amino acids P349, D355, F412, I438, K443, K465, and I467 of an EGFr polypeptide.

The term "agent" is used herein to denote a protein, polypeptide, peptide, nucleic acid, polynucleotide, oligonucleotide, carbohydrate, lipid, or a small molecule compound.

As used herein, the term "label" refers to any molecule that can be detected. In a certain embodiment, an antibody may be labeled by incorporation of a radiolabeled amino acid. In a certain embodiment, biotin moieties that can be detected by marked avidin (e.g., streptavidin containing a fluorescent marker or enzymatic activity that can be detected by optical or colorimetric methods) may be attached to the antibody. In certain embodiments, a label may be incorporated into or attached to another reagent which in turn binds to the antibody of interest. For example, a label may be incorporated into or attached to an antibody that in turn specifically binds the antibody of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Examples of labels for polypeptides include, but are not limited to, the following:radioisotopes or radionucleotides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., fluorescein isothocyanate (FITC), rhodamine, lanthanide phosphors, phycoerythrin (PE)), enzymatic labels (e.g., horseradish peroxidase, β-galactosidase, luciferase, alkaline phosphatase, glucose oxidase, glucose-6-phosphate dehydrogenase, alcohol dehyrogenase, malate dehyrogenase, penicillinase, luciferase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. As used herein, a therapeutic effect may or may not include a prophylactic effect.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents. In certain embodiments, an antineoplastic agent is panitumumab.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolecular species present in the composition. In certain embodiments, the object species is purified to essential homogeneity (contaminant species cannot be detected in the composition by conventional detection methods) wherein the composition consists essentially of a single macromolecular species.

The term patient includes human and animal subjects.

The term "disease state" refers to a physiological state of a cell or of a whole mammal in which an interruption, cessation, or disorder of cellular or body functions, systems, or organs has occurred.

The terms "treat" or "treatment" refer to both therapeutic treatment and prophylactic (or preventative) measures. In various embodiments, the object of treatment is to prevent or slow down (lessen) an undesired physiological change or disorder, such as the development or spread of cancer. Certain exemplary desired clinical results from treatment include, but are not limited to, alleviation of symptoms, diminishment of extent of disease, stabilized (i.e., not worsening) state of disease, delay or slowing of disease progression, amelioration or palliation of the disease state, remission (whether partial or total), and prevention of onset of disease. In certain embodiments, "treatment" can also mean prolonging survival as compared to expected survival if not receiving treatment. Those in need of treatment include those already with the condition or disorder as well as those prone to have the condition or disorder or those in which the condition or disorder is to be prevented.

The term "responsive" as used herein means that a patient or tumor shows a complete response or a partial response after administering an agent, according to RECIST (Response Evaluation Criteria in Solid Tumors). The term "nonresponsive" as used herein means that a patient or tumor shows stable disease or progressive disease after administering an agent, according to RECIST. RECIST is described, e.g., in Therasse et al., February 2000, "New Guidelines to Evaluate the Response to Treatment in Solid Tumors," J. Natl. Cancer Inst. 92(3):205-216, which is incorporated by reference herein in its entirety. Exemplary agents include, but are not limited to, specific binding agents to an EGFr polypeptide, including but not limited to, antibodies to EGFr.

A "disorder" is any condition that would benefit from one or more treatments. This includes chronic and acute disorders or disease including those pathological conditions which predispose the mammal to the disorder in question. Non-limiting examples of disorders to be treated herein include benign and malignant tumors, leukemias, and lymphoid malignancies, in particular breast, rectal, ovarian, stomach, endometrial, salivary gland, kidney, colon, thyroid, pancreatic, prostate, and bladder cancer. In certain embodiments, a disorder to be treated is a malignant tumor, such as cervical carcinomas and cervical intraepithelial squamous and glandular neoplasia, renal cell carcinoma (RCC), esophageal tumors, and carcinoma-derived cell lines.

A "disease or condition related to an EGFr polypeptide" includes one or more of the following:a disease or condition caused by an EGFr polypeptide; a disease or condition contributed to by an EGFr polypeptide; and a disease or condition that is associated with the presence of an EGFr polypeptide. In certain embodiments, a disease or condition related to an EGFr polypeptide is a cancer. Exemplary cancers include, but are not limited to, non small cell lung carcinoma, breast, colon, gastric, brain, bladder, head and neck, ovarian, and prostate carcinomas.

In "combined therapy," patients are treated with a first specific binding agent for a target antigen in combination with a second specific binding agent for the target antigen and/or a chemotherapeutic or antineoplastic agent and/or radiation therapy. In certain embodiments, combined therapy comprises at least a first specific binding agent and a second specific binding agent. In certain embodiments, the first and second specific binding agents are agents that specifically bind to an EGFr polypeptide. In certain embodiments, the first specific binding agent is panitumumab and the second specific binding agent is an agent that binds at least a portion of a panitumumab epitope on an EGFr polypeptide. In certain embodiments, the first specific binding agent is panitumumab and the second specific binding agent is an agent that does not bind to a panitumumab epitope on an EGFr polypeptide. Protocol designs will address effectiveness as assessed by reduction in tumor mass as well as the ability to reduce usual doses of standard chemotherapy. These dosage reductions will allow additional and/or prolonged therapy by reducing dose-related toxicity of the chemotherapeutic agent.

"Monotherapy" refers to the treatment of a disorder by administering immunotherapy to patients without an accompanying chemotherapeutic or antineoplastic agent. In certain embodiments, monotherapy comprises administering a specific binding agent for a target antigen. In certain embodiments, a specific binding agent used in monotherapy binds a panitumumab epitope on an EGFr polypeptide. In certain embodiments, a specific binding agent used in monotherapy does not bind a panitumumab epitope on an EGFr polypeptide.

Certain Embodiments

Panitumumab is a fully human antibody that specifically binds to an EGFr polypeptide. Panitumumab (also known as antibody E7.6.3 and ABX-EGF) is described, e.g., in PCT Publication No. WO 98/50433 and in U.S. Pat. No. 6,235,883. Panitumumab prevents the formation of human epidermoid carcinoma A431 xenografts in athymic mice, and alse eradicates already-established A431 tumor xenografts. See, e.g., Yang et al., *Crit. Rev. Oncol. Hematol.* 38(1):17-23, 2001; and Yang et al., *Cancer Res.* 59(6):1236-43, 1999. Panitumumab has been approved by the FDA to treat patients with metastatic colorectal cancer.

Certain Methods for Selecting a Specific Binding Agent that Binds to at Least a Portion of a Panitumumab Epitope on an EGFr Polypeptide In certain embodiments, a method is provided for selecting a specific binding agent to an epidermal growth factor (EGFr) polypeptide. In certain embodiments, a specific binding agent is selected that binds to at least a portion of a panitumumab epitope on an EGFr polypeptide. A specific binding agent that binds to at least a portion of a panitumumab epitope on an EGFr, in certain embodiments, may possess one or more similar in vivo activities as panitumumab.

In certain embodiments, a specific binding agent that binds to at least a portion of a panitumumab epitope on an EGFr polypeptide is selected as follows: a) an EGFr polypeptide is contacted with a first aliquot of an agent; b) the affinity of the agent for the EGFr polypeptide is determined; c) a mutant EGFr polypeptide is contacted with a second aliquot of the agent, wherein the mutant EGFr polypeptide comprises at least one point mutation at at least one amino acid position selected from P349, D355, F412, I438, K443, K465, and I467; d) the affinity of the agent for the mutant EGFr polypeptide is determined; and e) the agent is selected if the affinity of the agent for the EGFr polypeptide is greater than the affinity of the agent for the mutant EGFr polypeptide. In certain embodiments, steps (a) and (c) are carried out simultaneously and/or steps (b) and (d) are carried out simultaneously. In various embodiments, step (a) is carried out before step (b) or step (b) is carried out before step (a). In certain embodiments, the amount and/or concentration of the agent used in step (a) is the same as the amount and/or concentration of the agent used in step (c). In certain embodiments, the same method is used to determine the affinity of the agent for the EGFr polypeptide and to determine the affinity of the agent for the mutant EGFr polypeptide. In various embodiments, the agent is selected if the affinity of the agent for the EGFr polypeptide is at least 2-fold, at least 3-fold, at least 5-fold, or at least 10-fold the affinity of the agent for the mutant EGFr polypeptide.

In certain embodiments, a specific binding agent that binds to at least a portion of a panitumumab epitope on an EGFr polypeptide is selected as follows: a) a first EGFr polypeptide is contacted with a first aliquot of an agent, wherein the first EGFr polypeptide comprises an L2 domain; b) the affinity of the agent for the first EGFr polypeptide is determined; c) a second EGFr polypeptide is contacted with a second aliquot of the agent, wherein the second EGFr polypeptide lacks an L2 domain; d) the affinity of the agent for the first EGFr polypeptide is determined; and e) the agent is selected if the affinity of the agent for the first EGFr polypeptide is greater than the affinity of the agent for the second EGFr polypeptide. In certain embodiments, steps (a) and (c) are carried out simultaneously and/or steps (b) and (d) are carried out simultaneously. In various embodiments, step (a) is carried out before step (b) or step (b) is carried out before step (a). In certain embodiments, the amount and/or concentration of the agent used in step (a) is the same as the amount and/or concentration of the agent used in step (c). In certain embodiments, the same method is used to determine the affinity of the agent for the first EGFr polypeptide and to determine the affinity of the agent for the second EGFr polypeptide. In various embodiments, the agent is selected if the affinity of the agent for the first EGFr polypeptide is at least 2-fold, at least 3-fold, at least 5-fold, or at least 10-fold the affinity of the agent for the second EGFr polypeptide.

Certain Methods for Selecting a Specific Binding Agent that does not Bind to a Panitumumab Epitope on an EGFr Polypeptide In certain embodiments, treating a patient with at least two specific binding agents to EGFr, wherein the specific binding agents bind to different epitopes on an EGFr polypeptide, may be more effective than treating a patient with only one specific binding agent to EGFr. See, e.g., Friedman et al., *PNAS*, 102:1915-1920 (2005). Thus, in certain embodiments, it may be desirable to select a specific binding agent to an EGFr polypeptide that does not bind to a panitumumab epitope on an EGFr polypeptide. In certain instances, the selected specific binding agent may then be administered as a combination therapy with panitumumab. Such combination therapy may, in certain embodiments, be more effective than panitumumab alone.

In certain embodiments, a method of selecting a specific binding agent to an epidermal growth factor receptor (EGFr) polypeptide is provided. In certain embodiments, the method selects a specific binding agent that does not bind to a panitumumab epitope on an EGFr polypeptide.

In certain embodiments, a specific binding agent that does not bind to a panitumumab epitope on an EGFr polypeptide is selected as follows: a) an EGFr polypeptide is contacted with a first aliquot of an agent; b) the affinity of the agent for the EGFr polypeptide is determined; c) a mutant EGFr polypeptide is contacted with a second aliquot of the agent, wherein the mutant EGFr polypeptide comprises at least one point mutation at least one amino acid position selected from P349, D355; F412, I438, K443, K465, and I467; d) the affinity of the agent for the mutant EGFr polypeptide is determined; and e) the agent is selected if the affinity of the agent for the EGFr polypeptide is similar to the affinity of the agent for the mutant EGFr polypeptide. In certain embodiments, steps (a) and (c) are carried out simultaneously and/or steps (b) and (d) are carried out simultaneously. In various embodiments, step (a) is carried out before step (b) or step (b) is carried out before step (a). In certain embodiments, the amount and/or concentration of the agent used in step (a) is the same as the amount and/or concentration of the agent used in step (c). In certain embodiments, the same method is used to determine the affinity of the agent for the EGFr polypeptide and to determine the affinity of the agent for the mutant EGFr polypeptide. In certain embodiments, the agent is selected if the affinity of the agent for the EGFr polypeptide is less than 2-fold different from the affinity of the agent for the mutant EGFr polypeptide.

In certain embodiments, a specific binding agent that does not bind to a panitumumab epitope on an EGFr polypeptide is selected as follows: a) a first EGFr polypeptide is contacted with a first aliquot of an agent, wherein the first polypeptide comprises an L2 domain; b) the affinity of the agent for the first EGFr polypeptide is determined; c) a second EGFr polypeptide is contacted with a second aliquot of the agent, wherein the second EGFr polypeptide lacks an L2 domain; d) the affinity of the agent for the second EGFr polypeptide is determined; and e) the agent is selected if the affinity of the agent for the first EGFr polypeptide is similar to the affinity of the agent for the second EGFr polypeptide. In certain embodiments, steps (a) and (c) are carried out simultaneously and/or steps (b) and (d) are carried out simultaneously. In various embodiments, step (a) is carried out before step (b) or step (b) is carried out before step (a). In certain embodiments, the amount and/or concentration of the agent used in step (a) is the same as the amount and/or concentration of the agent used in step (c). In certain embodiments, the same method is used to determine the affinity of the agent for the first EGFr polypeptide and to determine the affinity of the agent for the second EGFr polypeptide. In certain embodiments, the agent is selected if the affinity of the agent for the first EGFr polypeptide is less than 2-fold different from the affinity of the agent for the second EGFr polypeptide.

Certain Exemplary Methods of Determining Affinity

In various methods discussed herein, the affinity of an agent for an EGFr polypeptide and/or the affinity of an agent for a mutant EGFr polypeptide is determined. Certain methods of determining the affinity of an agent for a polypeptide are known in the art. One skilled in the art can select an appropriate method based on the particular application. Certain exemplary methods of determining affinity of an agent for a polypeptide include, but are not limited to, ELISA and RIA methods, BIAcore assays, Western blotting, flow cytometry methods, and equilibrium/solution methods, affinity selection-mass spectrometry (AS-MS), microchip-affinity capillary electrophoresis (MC-ACE), kinetic exclusion fluorescence immunoassay, Mesoscale Discovery (MSD) assays and other assays based on electrochemiluminescence (ECL), and cell-based reported assays using, e.g., luciferase or GFP. Certain exemplary methods of determining affinity of an agent are described, e.g., in Goldberg et al., *Curr Opin Immunol.* 5(2):278-81 (1993), Van Regenmortel, *Dev Biol (Basel)* 112:141-51 (2003), Geuijen et al., *J. Immunol. Methods* 302 (1-2):68-77 (2005), Annis et al., *Anal Chem.* 79(12):4538-42 (2007), Stettler et al., *Electrophoresis* 28(11):1832-8 (2007), Xie et al., *J. Immunol Methods* 304 (1-2):1-14 (2005).

In certain embodiments, a method of determining affinity produces a relative affinity measurement, which is expressed as an affinity relative to the affinity of a positive control and/or the affinity of a negative control. In certain embodiments, a method of determining affinity produces a binding constant, such as, for example, a $k_a$ and/or a $k_d$, and/or an equilibrium constant, such as, for example, a $K_D$. In certain embodiments, affinity is determined using a competition assay in which the concentration of a first agent is held constant while the concentration of a second agent is varied.

In certain embodiments, a method comprises at least one step that is carried out in a high-throughput format.

Certain Exemplary Agents

Certain exemplary agents include, but are not limited to, proteins, polypeptides, peptides, nucleic acids, polynucleotides, oligonucleotides, carbohydrates, lipids, and small molecule compounds. In certain embodiments, the agent is a protein. In certain embodiments, the agent is an antibody. In various embodiments, the method is carried out in a high-throughput manner using, e.g., a collection of antibodies. Certain collections are known in the art and include, but are not limited to, display libraries (e.g. phage, DNA, ribosomal), recombinant methods of recovering genetic sequences of antibody from B-cell populations (including, but not limited to, Selected Lymphocyte Antibody Method (SLAM™) and Omnicolonal™ antibody technology), collections of antibody sequences generated using random mutagenesis, and collections of antibodies produced by hybridomas. In various embodiments, one skilled in the art can select an appropriate antibody collection for use in the methods.

In certain embodiments, the agent is a polypeptide. In various embodiments, the method is carried out in a high-throughput manner using, e.g., a collection of polypeptides. Certain collections are known in the art and an appropriate library can be selected for use in the method by one skilled in the art.

In certain embodiments, the agent is a small molecule compound. In various embodiments, the method is carried out in a high-throughput manner using, e.g., a collection of small molecule compounds. Certain collections are known in the art and an appropriate library can be selected for use in the method by one skilled in the art.

Certain Exemplary EGFr Polypeptides and Mutant EGFr Polypeptides

In certain embodiments, an EGFr polypeptide used in the methods is an EGFr polypeptide that lacks a cytoplasmic domain. In certain embodiments, an EGFr polypeptide used in the methods is an EGFr polypeptide that lacks both a transmembrane domain and a cytoplasmic domain. In certain embodiments, an EGFr polypeptide used in the methods is an EGFr ECD polypeptide. In certain embodiments, an EGFr polypeptide used in the methods is an EGFr ECD polypeptide comprising at least one domain selected from a CR1 domain, an L1 domain, a CR2 domain, and an L2 domain. In certain embodiments, an EGFr ECD polypeptide used in the methods comprises an L1 domain, a CR1 domain, an L2 domain, and a CR2 domain. In certain embodiments, an L1 domain of an EGFr polypeptide has the amino acid sequence of SEQ ID NO: 4. In certain embodiments, a CR1 domain of an EGFr polypeptide has the amino acid sequence of SEQ ID NO: 5. In certain embodiments, an L2 domain of an EGFr polypeptide has the amino acid sequence of SEQ ID NO: 3. In certain embodiments, a CR2 domain of an EGFr polypeptide has the amino acid sequence of SEQ ID NO: 6. In certain embodiments, an EGFr polypeptide used in the methods is a an EGFr ECD polypeptide comprising an L2 domain. In certain embodiments, an EGFr polypeptide used in the methods is an EGFr ECD polypeptide lacking an L2 domain.

In various embodiments, an EGFr polypeptide used in the methods comprises an amino acid sequence selected from any of SEQ ID NOs:1 to 8 and 13 to 15.

In certain embodiments, an amino acid substitution (or "point mutation") is made to an EGFr polypeptide to make a mutant EGFr polypeptide that is predicted to have a lower binding affinity for panitumumab than the EGFr polypeptide. In certain embodiments, the amino acid substitution is made at one or more amino acid positions selected from P349, D355, F412, I438, K443, K465, and I467 of an EGFr polypeptide. In certain embodiments, an amino acid substitution replaces a non-alanine amino acid with an alanine. In certain embodiments, a conservative amino acid substitution is made. In various embodiments, the affinity of panitumumab for a mutant EGFr polypeptide is reduced by at least 50%, at least 60%, at least 70%, at least 80%, at least 85%, at least 90%, or at least 95% relative to the affinity of panitumumab for an EGFr polypeptide.

In various embodiments, the affinity of a specific binding agent for a mutant EGFr polypeptide is reduced by at least 50%, at least 60%, at least 70%, at least 80%, at least 85%, at least 90%, or at least 95% relative to the affinity of the specific binding agent for an EGFr polypeptide. In various embodiments, the affinity of a specific binding agent for a mutant EGFr polypeptide is less than 50%, less than 40%, less than 30%, less than 25%, less than 20%, less than 15%, less than 10%, or less than 5% the affinity of the specific binding agent for an EGFr polypeptide. In certain embodiments, the affinity of a specific binding agent for a mutant EGFr polypeptide is reduced by less than 50% relative to the affinity of the specific binding agent for an EGFr polypeptide.

In certain embodiments, a mutant EGFr polypeptide used in the methods lacks a cytoplasmic domain. In certain embodiments, a mutant EGFr polypeptide used in the methods lacks both a transmembrane domain and a cytoplasmic domain. In certain embodiments, a mutant EGFr polypeptide used in the methods is a mutant EGFr ECD polypeptide. In certain embodiments, a mutant EGFr polypeptide used in the methods comprises an L2 domain. In certain embodiments, a mutant EGFr polypeptide used in the methods comprises at least one point mutation at least one amino acid position selected from P349, D355, F412, I438, K443, K465, and I467. In certain embodiments, a mutant EGFr polypeptide comprises at least one point mutation selected from P349A, D355T, F412A, and I438K.

In various embodiments, a mutant EGFr polypeptide used in the methods comprises an amino acid sequence selected from any of SEQ ID NOs:1 to 3, 8, and 13 to 15 having at least one point mutation at least one amino acid position selected from P349, D355, F412, I438, K443, K465, and I467. In various embodiments, a mutant EGFr polypeptide comprises an amino acid sequence selected from SEQ ID NOs:9 to 12 and 21 to 23.

EXAMPLES

Example 1

Testing Panitumumab Binding to EGFR Extracellular Domain and EGFR Extracellular Domain Truncations The following human EGFr polypeptides were separately expressed as avidin fusion proteins (with chicken avidin fused to the amino-terminus of the EGFr protein fragment) in transiently-transfected 293T cells using mammalian expression vector pCEP4 (Invitrogen):EGFr ECD (SEQ ID NO: 2), EGFr L1 domain (SEQ ID NO: 4), EGFr CR1 domain (SEQ ID NO: 5), EGFr L2 domain (SEQ ID NO: 3), EGFr CR2 domain (SEQ ID NO: 6), EGFr L1+CR1 domains (SEQ ID No: 7), and EGFr L1+CR1+L2 domains (SEQ ID NO: 8).

The EGFr polypeptide-avidin fusions were captured on biotin-coated polystyrene beads. Each of the captured EGFr polypeptide-avidin fusions was then incubated with 1 μg/ml panitumumab for one hour at room temperature in 200 μl 0.5% BSA in PBS. The captured EGFr polypeptide-avidin fusions were then incubated with an allophycocyanin (APC)-conjugated anti-human IgG secondary antibody (Vector Laboratories, Burlingame, Calif.) to detect binding of panitumumab to the EGFr polypeptide-avidin fusions and a FITC conjugated anti-avidin antibody (Jackson Immunoresearch Labs) to detect the avidin portion of the EGFr polypeptide-avidin fusions, for 30 minutes at room temperature in 200 μl 0.5% BSA in PBS.

Binding of panitumumab to the EGFr polypeptide-avidin fusions was detected by detecting the APC-conjugated anti-human IgG secondary antibody by flow cytometry. The EGFr polypeptide-avidin fusions were detected by detecting the FITC conjugated anti-avidin antibody by flow cytometry. The results of that experiment are shown in FIGS. 2A and 2B. Those figures shows that panitumumab bound to the EGFr ECD, the EGFr L2 domain, and the EGFr L1+CR1+L2 domains. Those results suggest that panitumumab bound to the L2 domain of EGFr.

Example 2

Testing Panitumumab Binding to EGFR L2 Domain Point Mutants

To determine what amino acids within the EGFr L2 domain are important for panitumumab binding, the following human EGFr L2 domain point mutants ("mutant EGFr L2 polypeptides") were separately expressed as avidin fusion proteins (with chicken avidin fused to the amino-terminus of the EGFr protein fragment) in transiently-transfected 293T cells using mammalian expression vector pCEP4 (Invitrogen):EGFr L2 P349A polypeptide (SEQ ID NO: 9), EGFr L2 R353A polypeptide (SEQ ID NO: 16), EGFr L2 D355T polypeptide (SEQ ID NO: 10), EGFr L2 F357A polypeptide (SEQ ID NO: 17), EGFr L2 Q384A polypeptide (SEQ ID NO: 18), EGFr L2 Q408M polypeptide (SEQ ID NO: 19), EGFr L2H409E polypeptide (SEQ ID NO: 20), EGFr L2 F412A polypeptide (SEQ ID NO: 11), EGFr L2 I438A polypeptide (SEQ ID NO: 12), EGFr L2 K443A polypeptide (SEQ ID NO: 21), EGFr L2 K465A polypeptide (SEQ ID NO: 22), EGFr L2 I467A polypeptide (SEQ ID NO: 23), EGFr L2 N473A polypeptide (SEQ ID NO: 24), EGFr L2 D355T/F357A polypeptide (SEQ ID NO: 25), and EGFr L2 Q408M/H409E polypeptide (SEQ ID NO: 26).

The mutant EGFr polypeptide-avidin fusions were captured on biotin-coated polystyrene beads. Each of the captured mutant EGFr polypeptide-avidin fusions was then incubated with 1 μg/ml panitumumab for one hour at room temperature in 200 μl 0.5% BSA in PBS. The captured mutant EGFr polypeptide-avidin fusions were then incubated with an allophycocyanin (APC)-conjugated anti-human IgG secondary antibody (Jackson Immunoresearch Labs) to detect binding of panitumumab to the mutant EGFr polypeptide-avidin fusions and a FITC conjugated anti-avidin antibody (Vector Laboratories, Burlingame, Calif.) to detect the avidin portion of the mutant EGFr polypeptide-avidin fusions, for 30 minutes at room temperature in 200 μl 0.5% BSA in PBS.

Figure 3:
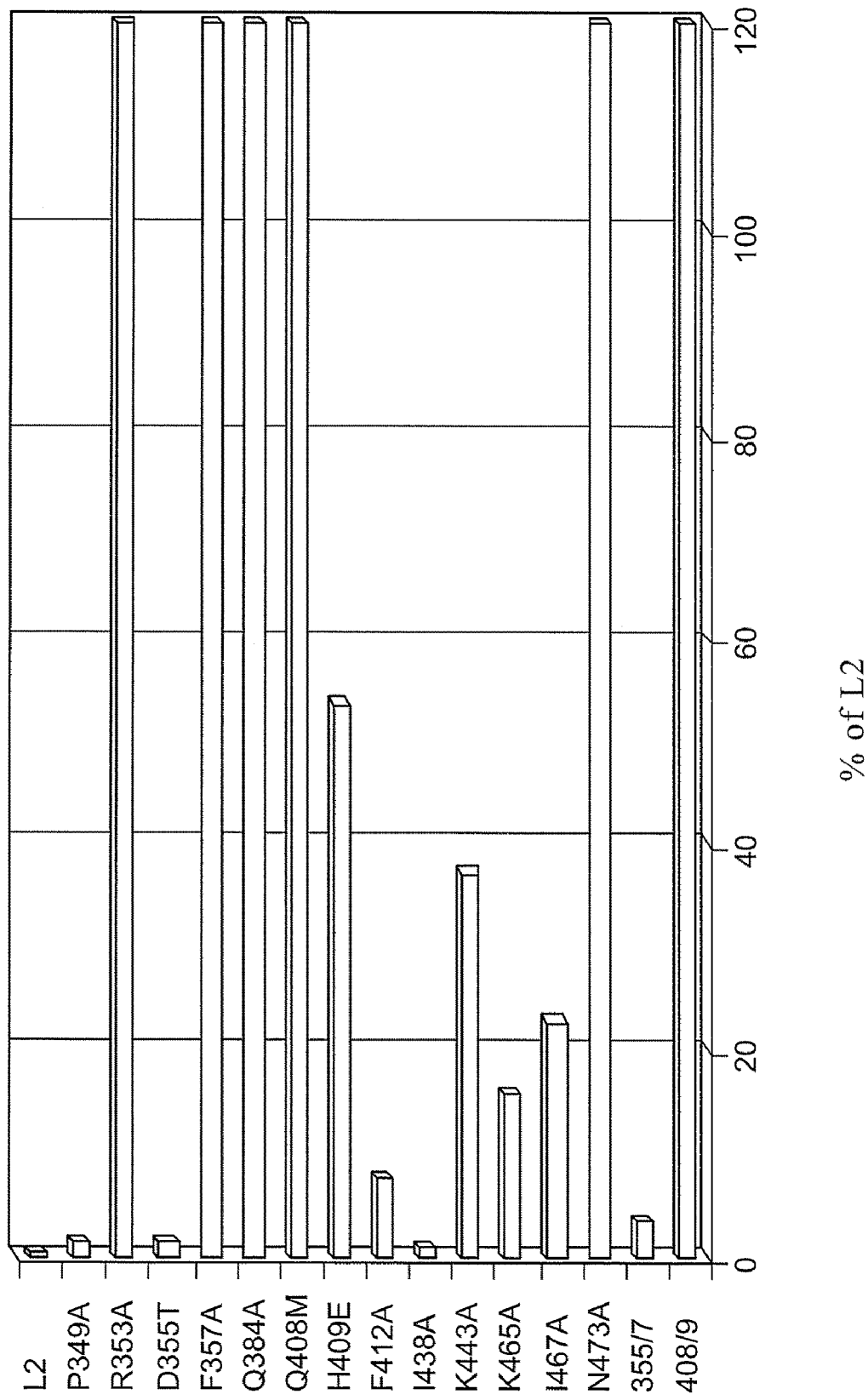
FIG. 3 shows a bar graph summarizing the binding of panitumumab to certain EGFr L2 domain point mutations, as described in Example 2.
Figure 4:
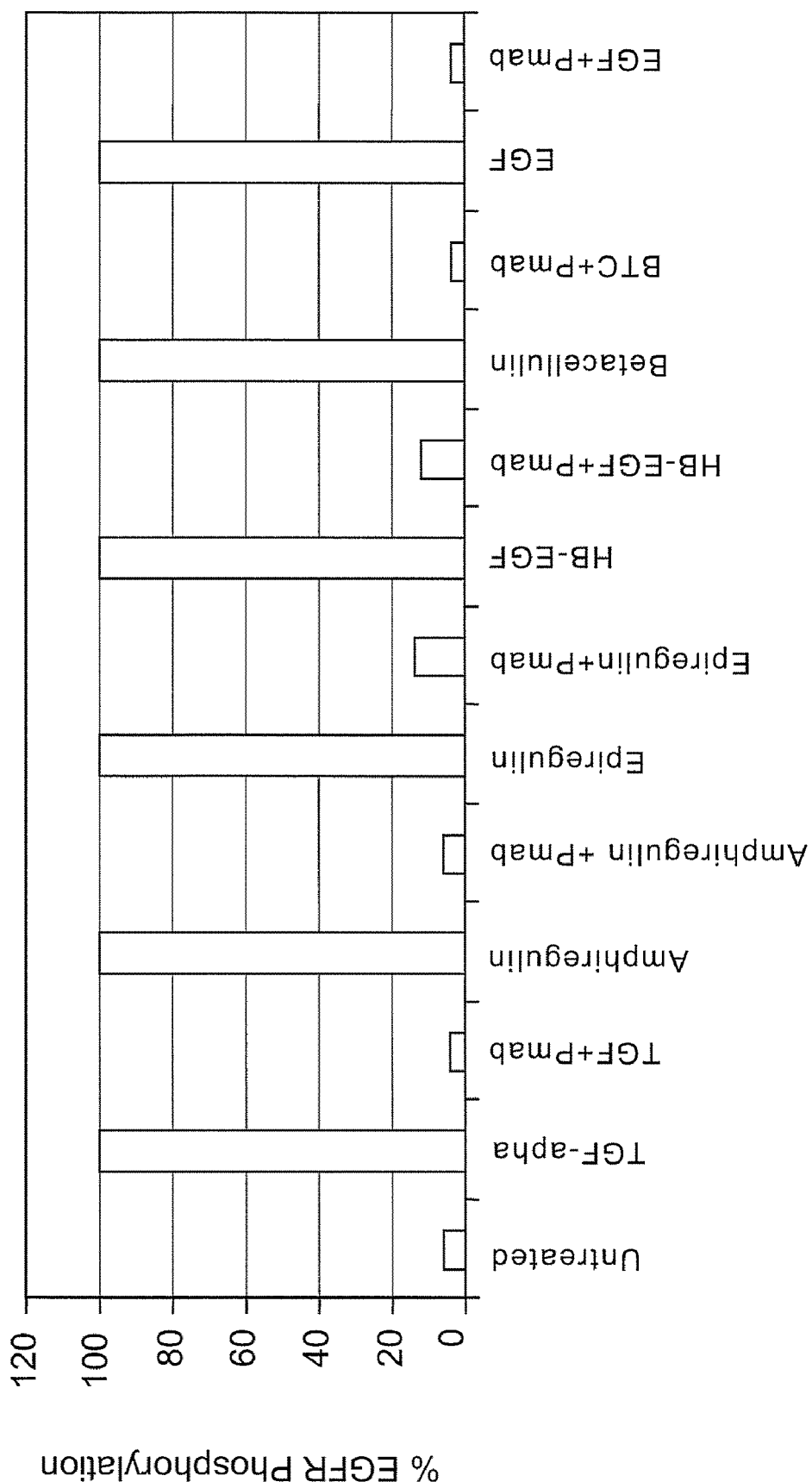
FIG. 4 shows a bar graph indicating panitumumab inhibition of EGFr activation by certain ligands, as described in Example 3.

Binding of panitumumab to the mutant EGFr L2 polypeptide-avidin fusions was detected by detecting the APC-conjugated anti-human IgG secondary antibody by flow cytometry. The mutant EGFr L2 polypeptide-avidin fusions were detected by detecting the FITC conjugated anti-avidin antibody by flow cytometry. The results of that experiment are shown as a bar graph in FIG. 3, which shows the identity of the mutant EGFr L2 polypeptide-avidin fusions on the x-axis, and the % binding of the mutant EGFr L2 polypeptide-avidin fusions to panitumumab, expressed as a percentage of wild-type EGFr polypeptide-avidin fusion binding to panitumumab, on the y-axis. The y-axis in FIG. 3 is a logarithmic scale.

In that experiment, the mutant EGFr L2 P349A polypeptide-avidin fusion, the mutant EGFr L2 D355T polypeptide-avidin fusion, the mutant EGFr L2 F412A polypeptide-avidin fusion, and the mutant EGFr L2 I438A polypeptide-avidin fusion did not bind panitumumab as strongly as the wild-type EGFr L2 polypeptide-avidin fusion or the other point mutants tested. The EGFr L2 domain P349A point mutation and the EGFr L2 domain D355T point mutatation each reduced panitumumab binding by 98%. The EGFr L2 domain F412A point mutation reduced panitumumab binding by 92%. The EGFr L2 domain I438A point mutation reduced panitumumab binding by 99%. The EGFr L2 domain K443A point mutation reduced panitumumab binding by 63%. The EGFr L2 domain K465A point mutation reduced panitumumab binding by 84%. The EGFr L2 domain 1467A point mutation reduced panitumumab binding by 77%. Those results suggest that the panitumumab epitope on EGFr includes amino acids P349, D355, F412, I438, K443, K465, and I467.

Three commercial antibodies were also tested for binding to certain mutant EGFr polypeptides by a similar method as described above (data not shown). Two of the three antibodies had a significantly different binding profile from panitumumab. For example, Upstate Biotechnology's EGFr antibody clone LA22 did not bind to the mutant EGFr L2 F357A polypeptide and did bind to the mutant EGFr L2 K443A polypeptide. Lab Vision's EGFr antibody clone 528 did not bind to the mutant EGFr L2 N473A polypeptide. Lab Vision's EGFr antibody clone B1D8 had a similar profile to panitumumab.

Example 3

Panitumumab Inhibition of Ligand-Induced EGFR Activation

To determine whether panitumumab inhibits EGFr activation by certain ligands, A549 non-small cell lung carcinoma (NSCLC) cells were treated with 20 mg/ml panitumumab for 1 hour and then separately stimulated for 15 minutes with each of the following EGFr ligands:TGF-α (10 ng/ml), amphiregulin (500 ng/ml), epiregulin (200 ng/ml), HB-EGF (200 ng/ml), betacellulin (10 ng/ml), and EGF (10 ng/ml). Inhibition of ligand-induced phosphorylation of EGFr was determined using an antibody that specifically binds to EGFr having a phosphate on tyrosine 1068 (pY1068) (Cell Signaling Technology, Beverly, Mass.).

The results of that experiment are shown in FIG. 4. In that experiment, panitumumab ("pmab") inhibited ligand-induced phosphorylation by all of the EGFr ligands tested by at least 87%.

TABLE 2

Table of Sequences

| Description | SEQ ID NO: | Sequence |
|---|---|---|
| human EGFr, Genbank AAX41033, without 24 amino acid leader sequence | 1 | leekkv cqgtsnkltq lgtfedhfls lqrmfnncev<br>vlgnleityv qrnydlsflk tiqevagyvl ialntverip<br>lenlqiirgn myyensyala vlsnydankt glkelpmrnl<br>qeilhgavrf snnpalcnve siqwrdivss dflsnmsmdf<br>qnhlgscqkc dpscpngscw gageencqkl tkiicaqqcs<br>grcrgkspsd cchnqcaagc tgpresdclv crkfrdeatc<br>kdtcpplmly npttyqmdvn pegkysfgat cvkkcprnyv<br>vtdhgscvra cgadsyemee dgvrkckkce gpcrkvcngi<br>gigefkdsls inatnikhfk nctsisgdlh ilpvafrgds<br>fthtppldpq eldilktvke itgflliqaw penrtdlhaf<br>enleiirgrt kqhgqfslav vslnitslgl rslkeisdgd<br>viisgnknlc yantinwkkl fgtsgqktki isnrgensck<br>atgqvchalc spegcwgpep rdcvscrnvs rgrecvdkcn<br>llegeprefv enseciqchp eclpqamnit ctgrgpdnci<br>qcahyidgph cvktcpagvm genntlvwky adaghvchlc<br>hpnctygctg pglegcptng pkipsiatgm vgalllllvv<br>algiglfmrr rhivrkrtlr rllqerelve pltpsgeapn<br>qallrilket efkkikvlgs gafgtvykgl wipegekvki<br>pvaikelrea tspkankeil deayvmasvd nphvcrllgi<br>cltstvqlit qlmpfgclld yvrehkdnig sqyllnwcvq<br>iakgmnyled rrlvhrdlaa rnvlvktpqh vkitdfglak<br>llgaeekeyh aeggkvpikw malesilhri ythqsdvwsy<br>gvtvwelmtf gskpydgipa seissilekg erlpqppict<br>idvymimvkc wmidadsrpk freliiefsk mardpqrylv<br>iqgdermhlp sptdsnfyra lmdeedmddv vdadeylipq<br>qgffsspsts rtpllsslsa tsnnstvaci drnglqscpi<br>kedsflqrys sdptgalted siddtflpvp eyinqsvpkr<br>pagsvqnpvy hngplnpaps rdphyqdphs tavgnpeyln<br>tvqptcvnst fdspahwaqk gshqisldnp dyqqdffpke<br>akpngifkgs taenaeylrv apqssefiga l |
| human EGFr extracellular domain, amino acids 1 to 621 | 2 | leekkv cqgtsnkltq lgtfedhfls lqrmfnncev<br>vlgnleityv qrnydlsflk tiqevagyvl ialntverip<br>lenlqiirgn myyensyala vlsnydankt glkelpmrnl<br>qeilhgavrf snnpalcnve siqwrdivss dflsnmsmdf<br>qnhlgscqkc dpscpngscw gageencqkl tkiicaqqcs<br>grcrgkspsd cchnqcaagc tgpresdclv crkfrdeatc<br>kdtcpplmly npttyqmdvn pegkysfgat cvkkcprnyv<br>vtdhgscvra cgadsyemee dgvrkckkce gpcrkvcngi<br>gigefkdsls inatnikhfk nctsisgdlh ilpvafrgds<br>fthtppldpq eldilktvke itgflliqaw penrtdlhaf<br>enleiirgrt kqhgqfslav vslnitslgl rslkeisdgd<br>viisgnknlc yantinwkkl fgtsgqktki isnrgensck<br>atgqvchalc spegcwgpep rdcvscrnvs rgrecvdkcn<br>llegeprefv enseciqchp eclpqamnit ctgrgpdnci<br>qcahyidgph cvktcpagvm genntlvwky adaghvchlc<br>hpnctygctg pglegcptng pkips |

TABLE 2-continued

Table of Sequences

| Description | SEQ ID NO: | Sequence |
|---|---|---|
| human EGFr L2 domain | 3 | kvcngi gigefkdsls inatnikhfk nctsisgdlh ilpvafrgds fthtppldpq eldilktvke itgflliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L1 domain | 4 | leekkv cqgtsnkltq lgtfedhfls lqrmfnncev vlgnleityv qrnydlsflk tiqevagyvi ialntverip lenlqiirgn myyensyala vlsnydankt glkelpmrnl qeilhgavrf snnpalcnve siqwrdivss dflsnmsmdf qnhlgscqkc dpscpngscw gageencqkl |
| human EGFr CR1 domain | 5 | tkiicaqqcs grcrgkspsd cchnqcaagc tgpresdclv crkfrdeatc kdtcpplmly npttyqmdvn pegkysfgat cvkkcprnyv vtdhgscvra cgadsyemee dgvrkckkce gpcr |
| human EGFr CR2 domain | 6 | crnvs rgrecvdkcn llegeprefv enseciqchp eclpqamnit ctgrgpdnci qcahyidgph cvktcpagvm genntlvwky adaghvchlc hpnctygctg pglegcptng pkips |
| human EGFr L1 + CR1 domains | 7 | leekkv cqgtsnkltq lgtfedhfls iqrmfnncev vlgnleityv qrnydlsflk tiqevagyvl ialntverip lenlqiirgn myyensyala vlsnydankt glkelpmrnl qeilhgavrf snnpalcnve siqwrdivss dflsnmsmdf qnhlgscqkc dpscpngscw gageencqkl tkiicaqqcs grcrgkspsd cchnqcaagc tgpresdclv crkfrdeatc kdtcpplmly npttyqmdvn pegkysfgat cvkkcprnyv vtdhgscvra cgadsyemee dgvrkckkce gpcr |
| human EGFr L1 + CR1 + L2 domains | 8 | leekkv cqgtsnkltq lgtfedhfls lqrmfnncev vlgnleityv qrnydlsflk tiqevagyvl ialntverip lenlqiirgn myyensyala vlsnydankt glkelpmrnl qeilhgavrf snnpalcnve siqwrdivss dflsnmsmdf qnhlgscqkc dpscpngscw gageencqkl tkiicaqqcs grcrgkspsd cchnqcaagc tgpresdclv crkfrdeatc kdtcpplmly npttyqmdvn pegkysfgat cvkkcprnyv vtdhgscvra cgadsyemee dgvrkckkce gpcrkvcngi gigefkdsls inatnikhfk nctsisgdlh ilpvafrgds fthtppldpq eldilktvke itgflliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain P349A point mutant | 9 | kvcngi gigefkdsls inatnikhfk nctsisgdlh ilavafrgds fthtppldpq eldilktvke itgflliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain D355T point mutant | 10 | kvcngi gigefkdsls inatnikhfk nctsisgdlh ilpvafrgts fthtppldpq eidilktvke itgflliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain F412A point mutant | 11 | kvcngi gigefkdsls inatnikhfk nctsisgdlh ilpvafrgds fthtppldpq eldilktvke itgflliqaw penrtdlhaf enleiirgrt kqhgqaslav vslnitslgl rslkeisdgd viisgnknlc yantinwkkl fgtsgqktki isnrgensck atgqvchalc spegcwgpep rdcvs |
| human EGFr L2 domain I438A point mutant | 12 | kvcngi gigefkdsls inatnikhfk nctsisgdlh ilpvafrgds fthtppldpq eldilktvke itgflliqaw penrtdlhaf enleiirgrt kqhgqfslav vslnitslgl rslkeisdgd vaisgnknlc yantinwkkl fgtsgqktki isnrgensck atgqvchalc spegcwgpep rdcvs |
| human EGFr CR1 + L2 | 13 | tkiicaqqcs grcrgkspsd cchnqcaagc tgpresdclv crkfrdeatc kdtcpplmly npttyqmdvn pegkysfgat cvkkcprnyv vtdhgscvra cgadsyemee dgvrkckkce gpcrkvcngi gigefkdsls inatnikhfk nctsisgdlh ilpvafrgds fthtppldpq eldilktvke itgflliqaw |

TABLE 2-continued

Table of Sequences

| Description | SEQ ID NO: | Sequence |
|---|---|---|
| | | penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 + CR2 | 14 | kvcngi gigefkdsls inatnikhfk nctsisgdlh ilpvafrgds fthtppldpq eldilktvke itgfllliqaw penrtdlhaf enleiirgrt kqhgqfslav vslnitslgl rslkeisdgd viisgnknlc yantinwkkl fgtsgqktki isnrgensck atgqvchalc spegcwgpep rdcvscrnvs rgrecvdkcn llegeprefv enseciqchp eclpqamnit ctgrgpdhci qcahyidgph cvktcpagvm genntlvwky adaghvchlc hpnctygctg pglegcptng pkips |
| human EGFr CR1 + L2 + CR2 | 15 | tkiicaqqcs grcrgkspsd cchnqcaagc tgpresdclv crkfrdeatc kdtcpplmly npttyqmdvn pegkysfgat cvkkcprnyv vtdhgscvra cgadsyemee dgvrkckkce gpcrkvcngi gigefkdsls inatnikhfk nctsisgdlh ilpvafrgds fthtppldpq eldilktvke itgfllliqaw penrtdlhaf enleiirgrt kqhgqfslav vslnitslgl rslkeisdgd viisgnknlc yantinwkkl fgtsgqktki isnrgensck atgqvchalc spegcwgpep rdcvscrnvs rgrecvdkcn llegeprefv enseciqchp eclpqamnit ctgrgpdnci qcahyidgph cvktcpagvm genntlvwky adaghvchlc hpnctygctg pglegcptng pkips |
| human EGFr L2 domain R353A point mutant | 16 | kvcngi gigefkdsls inatnikhfk nctsisgdlh ilpvafagds fthtppldpq eldilktvke itgfllliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain F357A point mutant | 17 | kvcngi gigefkdsls inatnikhfk nctsisgdlh ilpvafrgds athtppldpq eldilktvke itgfllliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain Q384A point mutant | 18 | kvcngi gigefkdsls inatnikhfk nctsisgdlh ilpvafrgds fthtppldpq eldilktvke itgfllliaaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain Q408M point mutant | 19 | kvcngi gigefkdsls inatnikhfk nctsisgdlh ilpvafrgds fthtppldpq eldilktvke itgfllliqaw penrtdlhaf enleiirgrt kmhgqfslav vslnitslgl rslkeisdgd viisgnknlc yantinwkkl fgtsgqktki isnrgensck atgqvchalc spegcwgpep rdcvs |
| human EGFr L2 domain H409E point mutant | 20 | kvcngi gigefkdsls inatnikhfk nctsisgdlh ilpvafrgds fthtppldpq eldilktvke itgfllliqaw penrtdlhaf enleiirgrt kqegqfslav vslnitslgl rslkeisdgd viisgnknlc yantinwkkl fgtsgqktki isnrgensck atgqvchalc spegcwgpep rdcvs |
| human EGFr L2 domain K443A point mutant | 21 | kvcngi gigefkdsls inatnikhfk nctsisgdlh ilpvafrgds fthtppldpq eldilktvke itgfllliqaw penrtdlhaf enleiirgrt kqhgqfslav vslnitslgl rslkeisdgd viisgnanlc yantinwkkl fgtsgqktki isnrgensck atgqvchalc spegcwgpep rdcvs |
| human EGFr L2 domain K465A point mutant | 22 | kvcngi gigefkdsls inatnikhfk nctsisgdlh ilpvafrgds fthtppldpq eldilktvke itgfllliqaw penrtdlhaf enleiirgrt kqhgqfslav vslnitslgl rslkeisdgd viisgnknlc yantinwkkl fgtsgqktai isnrgensck atgqvchalc spegcwgpep rdcvs |
| human EGFr L2 domain I467A point mutant | 23 | kvcngi gigefkdsls inatnikhfk nctsisgdlh ilpvafrgds fthtppldpq eldilktvke itgfllliqaw penrtdlhaf enleiirgrt kqhgqfslav vslnitslgl rslkeisdgd viisgnknlc yantinwkkl fgtsgqktki asnrgensck atgqvchalc spegcwgpep rdcvs |
| human EGFr L2 domain N473A | 24 | kvcngi gigefkdsls inatnikhfk nctsisgdlh ilpvafrgds fthtppldpq eldilktvke itgfllliqaw |

TABLE 2-continued

Table of Sequences

| Description | SEQ ID NO: | Sequence |
|---|---|---|
| point mutant | | penrtdihaf enleiirgrt kqhgqfslav vslnitslgl rslkeisdgd viisgnknlc yantinwkkl fgtsgqktki isnrgeasck atgqvchalc spegcwgpep rdcvs |
| human EGFr L2 domain D355T/F357A point mutant | 25 | kvcngi gigefkdsls inatnikhfk nctsisgdlh ilpvafrgts athtppldpq eldilktvke itgflliqaw penrtdlhaf enleiirgrt kqhgqfslav vslnitslgl rslkeisdgd viisgnknlc yantinwkkl fgtsgqktki isnrgensck atgqvchalc spegcwgpep rdcvs |
| human EGFr L2 domain Q408M/H409E point mutant | 26 | kvcngi gigefkdsls inatnikhfk nctsisgdlh ilpvafrgds fthtppldpq eldilktvke itgflliqaw penrtdlhaf enleiirgrt kmegqfslav vslnitslgl rslkeisdgd viisgnknlc yantinwkkl fgtsgqktki isnrgensck atgqvchalc spegcwgpep rdcvs |

We claim:

1. A method of selecting a specific binding agent to an epidermal growth factor receptor (EGFr) polypeptide, wherein the specific binding agent binds to at least a portion of a panitumumab epitope on an EGFr polypeptide, comprising:

a) contacting an EGFr polypeptide with an agent, wherein the EGFr polypeptide comprises the L2 domain of EGFr set forth in SEQ ID NO:3;

b) determining the affinity of the agent for the EGFr polypeptide;

c) contacting a mutant EGFr polypeptide with the agent, wherein the mutant EGFr polypeptide comprises at least one point mutation in at least one amino acid position selected from P349A, D355T, F412A, I438A, K443A, K465A, and I467A;

d) determining the affinity of the agent for the mutant EGFr polypeptide; and e) selecting the agent if the affinity for the EGFr polypeptide is at least 2-fold greater than the affinity for the mutant EGFr polypeptide.

2. The method of claim 1, wherein the mutant EGFr polypeptide is the same as the EGFr polypeptide except for the at least one mutation.

3. The method of claim 1, wherein the agent is selected from a protein, peptide, nucleic acid, carbohydrate, lipid, and small molecule compound.

4. The method of claim 3, wherein the agent is an antibody.

5. The method of claim 3, wherein the agent is a small molecule compound.

6. The method of claim 1, wherein the affinity for the EGFr polypeptide is at least 5-fold greater than the affinity for the mutant EGFr polypeptide.

7. The method of claim 1, wherein the affinity for the EGFr polypeptide is at least 10-fold greater than the affinity for the mutant EGFr polypeptide.

8. A method of selecting a specific binding agent to an epidermal growth factor receptor (EGFr) polypeptide, wherein the specific binding agent does not bind to a panitumumab epitope on an EGFr polypeptide (EGFr), comprising:

a) contacting an EGFr polypeptide with an agent, wherein the EGFr polypeptide comprises the L2 domain of EGFr set forth in SEQ ID NO:3;

b) determining the affinity of the agent for the EGFr polypeptide;

c) contacting a mutant EGFr polypeptide with the agent, wherein the mutant EGFr polypeptide comprises at least one point mutation in at least one amino acid position selected from P349A, D355T, F412A, I438A, K443A, K465A, and I467A;

d) determining the affinity of the agent for the mutant EGFr polypeptide; and e) selecting the agent if the affinity for the EGFr polypeptide is similar to the affinity for the mutant EGFr polypeptide.

9. The method of claim 8, wherein the mutant EGFr polypeptide is the same as the EGFr polypeptide except for the at least one mutation.

10. The method of claim 8, wherein the agent is selected from a protein, peptide, nucleic acid, carbohydrate, lipid, and small molecule compound.

11. The method of claim 10, wherein the agent is an antibody.

12. The method of claim 10, wherein the agent is a small molecule compound.

13. The method of claim 8, wherein there is less than a 2-fold difference between the affinity for the EGFr polypeptide and the affinity for the mutant EGFr polypeptide.

* * * * *

SEQUENCE LISTING

<160> NUMBER OF SEQ ID NOS: 26

<210> SEQ ID NO 1
<211> LENGTH: 1187
<212> TYPE: PRT
<213> ORGANISM: Homo sapiens

<400> SEQUENCE: 1

```
Leu Glu Glu Lys Lys Val Cys Gln Gly Thr Ser Asn Lys Leu Thr Gln
1               5                  10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220
```

```
Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
            245                 250                 255

Pro Glu Gly Lys Tyr Ser Phe Gly Ala Thr Cys Val Lys Lys Cys Pro
        260                 265                 270

Arg Asn Tyr Val Val Thr Asp His Gly Ser Cys Val Arg Ala Cys Gly
    275                 280                 285

Ala Asp Ser Tyr Glu Met Glu Glu Asp Gly Val Arg Lys Cys Lys Lys
290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser Ile Ala Thr
610                 615                 620

Gly Met Val Gly Ala Leu Leu Leu Leu Val Val Ala Leu Gly Ile Gly
625                 630                 635                 640

Gly Leu Phe Met Arg Arg Arg His Ile Val Arg Lys Arg Thr Leu Arg
                645                 650                 655
```

-continued

Arg Leu Leu Gln Glu Arg Glu Leu Val Glu Pro Leu Thr Pro Ser Gly
            660                 665                 670

Glu Ala Pro Asn Gln Ala Leu Leu Arg Ile Leu Lys Glu Thr Glu Phe
            675                 680                 685

Lys Lys Ile Lys Val Leu Gly Ser Gly Ala Phe Gly Thr Val Tyr Lys
690                 695                 700

Gly Leu Trp Ile Pro Glu Gly Lys Val Lys Ile Pro Val Ala Ile
705                 710                 715                 720

Lys Glu Leu Arg Glu Ala Thr Ser Pro Lys Ala Asn Lys Glu Ile Leu
            725                 730                 735

Asp Glu Ala Tyr Val Met Ala Ser Val Asp Asn Pro His Val Cys Arg
            740                 745                 750

Leu Leu Gly Ile Cys Leu Thr Ser Thr Val Gln Leu Ile Thr Gln Leu
            755                 760                 765

Met Pro Phe Gly Cys Leu Leu Asp Tyr Val Arg Glu His Lys Asp Asn
770                 775                 780

Ile Gly Ser Gln Tyr Leu Leu Asn Trp Cys Val Gln Ile Ala Lys Gly
785                 790                 795                 800

Met Asn Tyr Leu Glu Asp Arg Arg Leu Val His Arg Asp Leu Ala Ala
            805                 810                 815

Arg Asn Val Leu Val Lys Thr Pro Gln His Val Lys Ile Thr Asp Phe
            820                 825                 830

Gly Leu Ala Lys Leu Leu Gly Ala Glu Glu Lys Glu Tyr His Ala Glu
            835                 840                 845

Gly Gly Lys Val Pro Ile Lys Trp Met Ala Leu Glu Ser Ile Leu His
850                 855                 860

Arg Ile Tyr Thr His Gln Ser Asp Val Trp Ser Tyr Gly Val Thr Val
865                 870                 875                 880

Trp Glu Leu Met Thr Phe Gly Ser Lys Pro Tyr Asp Gly Ile Pro Ala
                885                 890                 895

Ser Glu Ile Ser Ser Ile Leu Glu Lys Gly Glu Arg Leu Pro Gln Pro
            900                 905                 910

Pro Ile Cys Thr Ile Asp Val Tyr Met Ile Met Val Lys Cys Trp Met
            915                 920                 925

Ile Asp Ala Asp Ser Arg Pro Lys Phe Arg Glu Leu Ile Ile Glu Phe
930                 935                 940

Ser Lys Met Ala Arg Asp Pro Gln Arg Tyr Leu Val Ile Gln Gly Asp
945                 950                 955                 960

Glu Arg Met His Leu Pro Ser Pro Thr Asp Ser Asn Phe Tyr Arg Ala
            965                 970                 975

Leu Met Asp Glu Glu Asp Met Asp Val Val Asp Ala Asp Glu Tyr
            980                 985                 990

Leu Ile Pro Gln Gln Gly Phe Phe Ser Ser Pro Ser Thr Ser Arg Thr
            995                 1000                1005

Pro Leu Leu Ser Ser Leu Ser Ala Thr Ser Asn Asn Ser Thr Val
    1010                1015                1020

Ala Cys Ile Asp Arg Asn Gly Leu Gln Ser Cys Pro Ile Lys Glu
    1025                1030                1035

Asp Ser Phe Leu Gln Arg Tyr Ser Ser Asp Pro Thr Gly Ala Leu
    1040                1045                1050

Thr Glu Asp Ser Ile Asp Asp Thr Phe Leu Pro Val Pro Glu Tyr
    1055                1060                1065

Ile Asn Gln Ser Val Pro Lys Arg Pro Ala Gly Ser Val Gln Asn

```
              1070            1075            1080
Pro Val Tyr His Asn Gln Pro Leu Asn Pro Ala Pro Ser Arg Asp
        1085            1090            1095
Pro His Tyr Gln Asp Pro His Ser Thr Ala Val Gly Asn Pro Glu
    1100            1105            1110
Tyr Leu Asn Thr Val Gln Pro Thr Cys Val Asn Ser Thr Phe Asp
    1115            1120            1125
Ser Pro Ala His Trp Ala Gln Lys Gly Ser His Gln Ile Ser Leu
    1130            1135            1140
Asp Asn Pro Asp Tyr Gln Gln Asp Phe Phe Pro Lys Glu Ala Lys
    1145            1150            1155
Pro Asn Gly Ile Phe Lys Gly Ser Thr Ala Glu Asn Ala Glu Tyr
    1160            1165            1170
Leu Arg Val Ala Pro Gln Ser Ser Glu Phe Ile Gly Ala Leu
    1175            1180            1185

<210> SEQ ID NO 2
<211> LENGTH: 621
<212> TYPE: PRT
<213> ORGANISM: Homo sapiens

<400> SEQUENCE: 2

Leu Glu Glu Lys Lys Val Cys Gln Gly Thr Ser Asn Lys Leu Thr Gln
1               5                   10                  15
Leu Gly Thr Phe Glu Asp His Phe Leu Ser Leu Gln Arg Met Phe Asn
            20                  25                  30
Asn Cys Glu Val Val Leu Gly Asn Leu Glu Ile Thr Tyr Val Gln Arg
        35                  40                  45
Asn Tyr Asp Leu Ser Phe Leu Lys Thr Ile Gln Glu Val Ala Gly Tyr
    50                  55                  60
Val Leu Ile Ala Leu Asn Thr Val Glu Arg Ile Pro Leu Glu Asn Leu
65                  70                  75                  80
Gln Ile Ile Arg Gly Asn Met Tyr Tyr Glu Asn Ser Tyr Ala Leu Ala
                85                  90                  95
Val Leu Ser Asn Tyr Asp Ala Asn Lys Thr Gly Leu Lys Glu Leu Pro
            100                 105                 110
Met Arg Asn Leu Gln Glu Ile Leu His Gly Ala Val Arg Phe Ser Asn
        115                 120                 125
Asn Pro Ala Leu Cys Asn Val Glu Ser Ile Gln Trp Arg Asp Ile Val
    130                 135                 140
Ser Ser Asp Phe Leu Ser Asn Met Ser Met Asp Phe Gln Asn His Leu
145                 150                 155                 160
Gly Ser Cys Gln Lys Cys Asp Pro Ser Cys Pro Asn Gly Ser Cys Trp
                165                 170                 175
Gly Ala Gly Glu Glu Asn Cys Gln Lys Leu Thr Lys Ile Ile Cys Ala
            180                 185                 190
Gln Gln Cys Ser Gly Arg Cys Arg Gly Lys Ser Pro Ser Asp Cys Cys
        195                 200                 205
His Asn Gln Cys Ala Ala Gly Cys Thr Gly Pro Arg Glu Ser Asp Cys
    210                 215                 220
Leu Val Cys Arg Lys Phe Arg Asp Glu Ala Thr Cys Lys Asp Thr Cys
225                 230                 235                 240
Pro Pro Leu Met Leu Tyr Asn Pro Thr Thr Tyr Gln Met Asp Val Asn
                245                 250                 255
Pro Glu Gly Lys Tyr Ser Phe Gly Ala Thr Cys Val Lys Lys Cys Pro
```

```
                    260                 265                 270
Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
        290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
            325                 330                 335

Asn Cys Thr Ser Ile Ser Gly Asp Leu His Ile Leu Pro Val Ala Phe
        340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
        370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
            405                 410                 415

Val Ser Leu Asn Ile Thr Ser Leu Gly Leu Arg Ser Leu Lys Glu Ile
        420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
        450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
            485                 490                 495

Arg Asp Cys Val Ser Cys Arg Asn Val Ser Arg Gly Arg Glu Cys Val
        500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
            565                 570                 575

Gly Glu Asn Asn Thr Leu Val Trp Lys Tyr Ala Asp Ala Gly His Val
        580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Pro Ser
        610                 615                 620

<210> SEQ ID NO 3
<211> LENGTH: 191
<212> TYPE: PRT
<213> ORGANISM: Homo sapiens

<400> SEQUENCE: 3

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
```

```
            20                  25                  30
Gly Asp Leu His Ile Leu Pro Val Ala Phe Arg Gly Asp Ser Phe Thr
            35                  40                  45
His Thr Pro Pro Leu Asp Pro Gln Glu Leu Asp Ile Leu Lys Thr Val
        50                  55                  60
Lys Glu Ile Thr Gly Phe Leu Leu Ile Gln Ala Trp Pro Glu Asn Arg
65                  70                  75                  80
Thr Asp Leu His Ala Phe Glu Asn Leu Glu Ile Ile Arg Gly Arg Thr
                85                  90                  95
Lys Gln His Gly Gln Phe Ser Leu Ala Val Val Ser Leu Asn Ile Thr
            100                 105                 110
Ser Leu Gly Leu Arg Ser Leu Lys Glu Ile Ser Asp Gly Asp Val Ile
            115                 120                 125
Ile Ser Gly Asn Lys Asn Leu Cys Tyr Ala Asn Thr Ile Asn Trp Lys
            130                 135                 140
Lys Leu Phe Gly Thr Ser Gly Gln Lys Thr Lys Ile Ile Ser Asn Arg
145                 150                 155                 160
Gly Glu Asn Ser Cys Lys Ala Thr Gly Gln Val Cys His Ala Leu Cys
                165                 170                 175
Ser Pro Glu Gly Cys Trp Gly Pro Glu Pro Arg Asp Cys Val Ser
            180                 185                 190

<210> SEQ ID NO 4
<211> LENGTH: 186
<212> TYPE: PRT
<213> ORGANISM: Homo sapiens

<400> SEQUENCE: 4

Leu Glu Glu Lys Lys Val Cys Gln Gly Thr Ser Asn Lys Leu Thr Gln
1               5                   10                  15
Leu Gly Thr Phe Glu Asp His Phe Leu Ser Leu Gln Arg Met Phe Asn
            20                  25                  30
Asn Cys Glu Val Val Leu Gly Asn Leu Glu Ile Thr Tyr Val Gln Arg
            35                  40                  45
Asn Tyr Asp Leu Ser Phe Leu Lys Thr Ile Gln Glu Val Ala Gly Tyr
        50                  55                  60
Val Leu Ile Ala Leu Asn Thr Val Glu Arg Ile Pro Leu Glu Asn Leu
65                  70                  75                  80
Gln Ile Ile Arg Gly Asn Met Tyr Tyr Glu Asn Ser Tyr Ala Leu Ala
                85                  90                  95
Val Leu Ser Asn Tyr Asp Ala Asn Lys Thr Gly Leu Lys Glu Leu Pro
            100                 105                 110
Met Arg Asn Leu Gln Glu Ile Leu His Gly Ala Val Arg Phe Ser Asn
            115                 120                 125
Asn Pro Ala Leu Cys Asn Val Glu Ser Ile Gln Trp Arg Asp Ile Val
            130                 135                 140
Ser Ser Asp Phe Leu Ser Asn Met Ser Met Asp Phe Gln Asn His Leu
145                 150                 155                 160
Gly Ser Cys Gln Lys Cys Asp Pro Ser Cys Pro Asn Gly Ser Cys Trp
                165                 170                 175
Gly Ala Gly Glu Glu Asn Cys Gln Lys Leu
            180                 185

<210> SEQ ID NO 5
<211> LENGTH: 124
<212> TYPE: PRT
```

-continued

<213> ORGANISM: Homo sapiens

<400> SEQUENCE: 5

```
Thr Lys Ile Ile Cys Ala Gln Gln Cys Ser Gly Arg Cys Arg Gly Lys
1               5                   10                  15
Ser Pro Ser Asp Cys Cys His Asn Gln Cys Ala Ala Gly Cys Thr Gly
            20                  25                  30
Pro Arg Glu Ser Asp Cys Leu Val Cys Arg Lys Phe Arg Asp Glu Ala
        35                  40                  45
Thr Cys Lys Asp Thr Cys Pro Pro Leu Met Leu Tyr Asn Pro Thr Thr
    50                  55                  60
Tyr Gln Met Asp Val Asn Pro Glu Gly Lys Tyr Ser Phe Gly Ala Thr
65                  70                  75                  80
Cys Val Lys Lys Cys Pro Arg Asn Tyr Val Val Thr Asp His Gly Ser
                85                  90                  95
Cys Val Arg Ala Cys Gly Ala Asp Ser Tyr Glu Met Glu Glu Asp Gly
            100                 105                 110
Val Arg Lys Cys Lys Lys Cys Glu Gly Pro Cys Arg
        115                 120
```

<210> SEQ ID NO 6
<211> LENGTH: 120
<212> TYPE: PRT
<213> ORGANISM: Homo sapiens

<400> SEQUENCE: 6

```
Cys Arg Asn Val Ser Arg Gly Arg Glu Cys Val Asp Lys Cys Asn Leu
1               5                   10                  15
Leu Glu Gly Glu Pro Arg Glu Phe Val Glu Asn Ser Glu Cys Ile Gln
            20                  25                  30
Cys His Pro Glu Cys Leu Pro Gln Ala Met Asn Ile Thr Cys Thr Gly
        35                  40                  45
Arg Gly Pro Asp Asn Cys Ile Gln Cys Ala His Tyr Ile Asp Gly Pro
    50                  55                  60
His Cys Val Lys Thr Cys Pro Ala Gly Val Met Gly Glu Asn Asn Thr
65                  70                  75                  80
Leu Val Trp Lys Tyr Ala Asp Ala Gly His Val Cys His Leu Cys His
                85                  90                  95
Pro Asn Cys Thr Tyr Gly Cys Thr Gly Pro Gly Leu Glu Gly Cys Pro
            100                 105                 110
Thr Asn Gly Pro Lys Ile Pro Ser
        115                 120
```

<210> SEQ ID NO 7
<211> LENGTH: 310
<212> TYPE: PRT
<213> ORGANISM: Homo sapiens

<400> SEQUENCE: 7

```
Leu Glu Glu Lys Lys Val Cys Gln Gly Thr Ser Asn Lys Leu Thr Gln
1               5                   10                  15
Leu Gly Thr Phe Glu Asp His Phe Leu Ser Leu Gln Arg Met Phe Asn
            20                  25                  30
Asn Cys Glu Val Val Leu Gly Asn Leu Glu Ile Thr Tyr Val Gln Arg
        35                  40                  45
Asn Tyr Asp Leu Ser Phe Leu Lys Thr Ile Gln Glu Val Ala Gly Tyr
    50                  55                  60
```

```
Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg
305                 310

<210> SEQ ID NO 8
<211> LENGTH: 501
<212> TYPE: PRT
<213> ORGANISM: Homo sapiens

<400> SEQUENCE: 8

Leu Glu Glu Lys Lys Val Cys Gln Gly Thr Ser Asn Lys Leu Thr Gln
 1               5                  10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125
```

```
Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
            195                 200                 205

His Asn Gln Cys Ala Ala Gly Cys Thr Gly Pro Arg Glu Ser Asp Cys
210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser
            500
```

<210> SEQ ID NO 9
<211> LENGTH: 191
<212> TYPE: PRT
<213> ORGANISM: Homo sapiens

<400> SEQUENCE: 9

-continued

```
Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Ala Val Ala Phe Arg Gly Asp Ser Phe Thr
            35                  40                  45

His Thr Pro Pro Leu Asp Pro Gln Glu Leu Asp Ile Leu Lys Thr Val
        50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 10
<211> LENGTH: 191
<212> TYPE: PRT
<213> ORGANISM: Homo sapiens

<400> SEQUENCE: 10

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Thr Ser Phe Thr
            35                  40                  45

His Thr Pro Pro Leu Asp Pro Gln Glu Leu Asp Ile Leu Lys Thr Val
        50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190
```

```
<210> SEQ ID NO 11
<211> LENGTH: 191
<212> TYPE: PRT
<213> ORGANISM: Homo sapiens

<400> SEQUENCE: 11

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Ala Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 12
<211> LENGTH: 191
<212> TYPE: PRT
<213> ORGANISM: Homo sapiens

<400> SEQUENCE: 12

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ala
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
```

```
                145                 150                 155                 160
Gly Glu Asn Ser Cys Lys Ala Thr Gly Gln Val Cys His Ala Leu Cys
                165                 170                 175
Ser Pro Glu Gly Cys Trp Gly Pro Glu Pro Arg Asp Cys Val Ser
                180                 185                 190

<210> SEQ ID NO 13
<211> LENGTH: 315
<212> TYPE: PRT
<213> ORGANISM: Homo sapiens

<400> SEQUENCE: 13

Thr Lys Ile Ile Cys Ala Gln Gln Cys Ser Gly Arg Cys Arg Gly Lys
1               5                   10                  15
Ser Pro Ser Asp Cys Cys His Asn Gln Cys Ala Ala Gly Cys Thr Gly
                20                  25                  30
Pro Arg Glu Ser Asp Cys Leu Val Cys Arg Lys Phe Arg Asp Glu Ala
                35                  40                  45
Thr Cys Lys Asp Thr Cys Pro Pro Leu Met Leu Tyr Asn Pro Thr Thr
        50                  55                  60
Tyr Gln Met Asp Val Asn Pro Glu Gly Lys Tyr Ser Phe Gly Ala Thr
65                  70                  75                  80
Cys Val Lys Lys Cys Pro Arg Asn Tyr Val Val Thr Asp His Gly Ser
                85                  90                  95
Cys Val Arg Ala Cys Gly Ala Asp Ser Tyr Glu Met Glu Glu Asp Gly
                100                 105                 110
Val Arg Lys Cys Lys Lys Cys Glu Gly Pro Cys Arg Lys Val Cys Asn
                115                 120                 125
Gly Ile Gly Ile Gly Glu Phe Lys Asp Ser Leu Ser Ile Asn Ala Thr
        130                 135                 140
Asn Ile Lys His Phe Lys Asn Cys Thr Ser Ile Ser Gly Asp Leu His
145                 150                 155                 160
Ile Leu Pro Val Ala Phe Arg Gly Asp Ser Phe Thr His Thr Pro Pro
                165                 170                 175
Leu Asp Pro Gln Glu Leu Asp Ile Leu Lys Thr Val Lys Glu Ile Thr
                180                 185                 190
Gly Phe Leu Leu Ile Gln Ala Trp Pro Glu Asn Arg Thr Asp Leu His
        195                 200                 205
Ala Phe Glu Asn Leu Glu Ile Ile Arg Gly Arg Thr Lys Gln His Gly
        210                 215                 220
Gln Phe Ser Leu Ala Val Val Ser Leu Asn Ile Thr Ser Leu Gly Leu
225                 230                 235                 240
Arg Ser Leu Lys Glu Ile Ser Asp Gly Asp Val Ile Ile Ser Gly Asn
                245                 250                 255
Lys Asn Leu Cys Tyr Ala Asn Thr Ile Asn Trp Lys Lys Leu Phe Gly
                260                 265                 270
Thr Ser Gly Gln Lys Thr Lys Ile Ile Ser Asn Arg Gly Glu Asn Ser
                275                 280                 285
Cys Lys Ala Thr Gly Gln Val Cys His Ala Leu Cys Ser Pro Glu Gly
                290                 295                 300
Cys Trp Gly Pro Glu Pro Arg Asp Cys Val Ser
305                 310                 315

<210> SEQ ID NO 14
<211> LENGTH: 311
<212> TYPE: PRT
```

<213> ORGANISM: Homo sapiens

<400> SEQUENCE: 14

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser Cys
            180                 185                 190

Arg Asn Val Ser Arg Gly Arg Glu Cys Val Asp Lys Cys Asn Leu Leu
        195                 200                 205

Glu Gly Glu Pro Arg Glu Phe Val Glu Asn Ser Glu Cys Ile Gln Cys
    210                 215                 220

His Pro Glu Cys Leu Pro Gln Ala Met Asn Ile Thr Cys Thr Gly Arg
225                 230                 235                 240

Gly Pro Asp Asn Cys Ile Gln Cys Ala His Tyr Ile Asp Gly Pro His
                245                 250                 255

Cys Val Lys Thr Cys Pro Ala Gly Val Met Gly Glu Asn Asn Thr Leu
            260                 265                 270

Val Trp Lys Tyr Ala Asp Ala Gly His Val Cys His Leu Cys His Pro
        275                 280                 285

Asn Cys Thr Tyr Gly Cys Thr Gly Pro Gly Leu Glu Gly Cys Pro Thr
    290                 295                 300

Asn Gly Pro Lys Ile Pro Ser
305                 310

<210> SEQ ID NO 15
<211> LENGTH: 435
<212> TYPE: PRT
<213> ORGANISM: Homo sapiens

<400> SEQUENCE: 15

Thr Lys Ile Ile Cys Ala Gln Gln Cys Ser Gly Arg Cys Arg Gly Lys
1               5                   10                  15

Ser Pro Ser Asp Cys Cys His Asn Gln Cys Ala Ala Gly Cys Thr Gly
            20                  25                  30

Pro Arg Glu Ser Asp Cys Leu Val Cys Arg Lys Phe Arg Asp Glu Ala
        35                  40                  45

Thr Cys Lys Asp Thr Cys Pro Pro Leu Met Leu Tyr Asn Pro Thr Thr
 50                  55                  60

Tyr Gln Met Asp Val Asn Pro Glu Gly Lys Tyr Ser Phe Gly Ala Thr
 65                  70                  75                  80

Cys Val Lys Lys Cys Pro Arg Asn Tyr Val Val Thr Asp His Gly Ser
                 85                  90                  95

Cys Val Arg Ala Cys Gly Ala Asp Ser Tyr Glu Met Glu Glu Asp Gly
            100                 105                 110

Val Arg Lys Cys Lys Lys Cys Glu Gly Pro Cys Arg Lys Val Cys Asn
        115                 120                 125

Gly Ile Gly Ile Gly Glu Phe Lys Asp Ser Leu Ser Ile Asn Ala Thr
130                 135                 140

Asn Ile Lys His Phe Lys Asn Cys Thr Ser Ile Ser Gly Asp Leu His
145                 150                 155                 160

Ile Leu Pro Val Ala Phe Arg Gly Asp Ser Phe Thr His Thr Pro Pro
                165                 170                 175

Leu Asp Pro Gln Glu Leu Asp Ile Leu Lys Thr Val Lys Glu Ile Thr
            180                 185                 190

Gly Phe Leu Leu Ile Gln Ala Trp Pro Glu Asn Arg Thr Asp Leu His
        195                 200                 205

Ala Phe Glu Asn Leu Glu Ile Ile Arg Gly Arg Thr Lys Gln His Gly
210                 215                 220

Gln Phe Ser Leu Ala Val Val Ser Leu Asn Ile Thr Ser Leu Gly Leu
225                 230                 235                 240

Arg Ser Leu Lys Glu Ile Ser Asp Gly Asp Val Ile Ile Ser Gly Asn
                245                 250                 255

Lys Asn Leu Cys Tyr Ala Asn Thr Ile Asn Trp Lys Lys Leu Phe Gly
            260                 265                 270

Thr Ser Gly Gln Lys Thr Lys Ile Ile Ser Asn Arg Gly Glu Asn Ser
        275                 280                 285

Cys Lys Ala Thr Gly Gln Val Cys His Ala Leu Cys Ser Pro Glu Gly
290                 295                 300

Cys Trp Gly Pro Glu Pro Arg Asp Cys Val Ser Cys Arg Asn Val Ser
305                 310                 315                 320

Arg Gly Arg Glu Cys Val Asp Lys Cys Asn Leu Leu Glu Gly Glu Pro
                325                 330                 335

Arg Glu Phe Val Glu Asn Ser Glu Cys Ile Gln Cys His Pro Glu Cys
            340                 345                 350

Leu Pro Gln Ala Met Asn Ile Thr Cys Thr Gly Arg Gly Pro Asp Asn
        355                 360                 365

Cys Ile Gln Cys Ala His Tyr Ile Asp Gly Pro His Cys Val Lys Thr
370                 375                 380

Cys Pro Ala Gly Val Met Gly Glu Asn Asn Thr Leu Val Trp Lys Tyr
385                 390                 395                 400

Ala Asp Ala Gly His Val Cys His Leu Cys His Pro Asn Cys Thr Tyr
                405                 410                 415

Gly Cys Thr Gly Pro Gly Leu Glu Gly Cys Pro Thr Asn Gly Pro Lys
            420                 425                 430

Ile Pro Ser
        435

<210> SEQ ID NO 16
<211> LENGTH: 191
<212> TYPE: PRT

<213> ORGANISM: Homo sapiens

<400> SEQUENCE: 16

```
Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Ala Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190
```

<210> SEQ ID NO 17
<211> LENGTH: 191
<212> TYPE: PRT
<213> ORGANISM: Homo sapiens

<400> SEQUENCE: 17

```
Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Ala Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175
```

```
Ser Pro Glu Gly Cys Trp Gly Pro Glu Pro Arg Asp Cys Val Ser
        180                 185                 190

<210> SEQ ID NO 18
<211> LENGTH: 191
<212> TYPE: PRT
<213> ORGANISM: Homo sapiens

<400> SEQUENCE: 18

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Ala Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
        180                 185                 190

<210> SEQ ID NO 19
<211> LENGTH: 191
<212> TYPE: PRT
<213> ORGANISM: Homo sapiens

<400> SEQUENCE: 19

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Met His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125
```

```
Ile Ser Gly Asn Lys Asn Leu Cys Tyr Ala Asn Thr Ile Asn Trp Lys
        130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 20
<211> LENGTH: 191
<212> TYPE: PRT
<213> ORGANISM: Homo sapiens

<400> SEQUENCE: 20

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln Glu Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 21
<211> LENGTH: 191
<212> TYPE: PRT
<213> ORGANISM: Homo sapiens

<400> SEQUENCE: 21

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
```

```
                 85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Ala Asn Leu Cys Tyr Ala Asn Thr Ile Asn Trp Lys
    130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 22
<211> LENGTH: 191
<212> TYPE: PRT
<213> ORGANISM: Homo sapiens

<400> SEQUENCE: 22

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
        115                 120                 125

Ile Ser Gly Asn Lys Asn Leu Cys Tyr Ala Asn Thr Ile Asn Trp Lys
    130                 135                 140

Lys Leu Phe Gly Thr Ser Gly Gln Lys Thr Ala Ile Ile Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 23
<211> LENGTH: 191
<212> TYPE: PRT
<213> ORGANISM: Homo sapiens

<400> SEQUENCE: 23

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45
```

-continued

His Thr Pro Pro Leu Asp Pro Gln Glu Leu Asp Ile Leu Lys Thr Val
            50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
            115                 120                 125

Ile Ser Gly Asn Lys Asn Leu Cys Tyr Ala Asn Thr Ile Asn Trp Lys
            130                 135                 140

Lys Leu Phe Gly Thr Ser Gly Gln Lys Thr Lys Ile Ala Ser Asn Arg
145                 150                 155                 160

Gly Glu Asn Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 24
<211> LENGTH: 191
<212> TYPE: PRT
<213> ORGANISM: Homo sapiens

<400> SEQUENCE: 24

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
            35                  40                  45

His Thr Pro Pro Leu Asp Pro Gln Glu Leu Asp Ile Leu Lys Thr Val
            50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
                85                  90                  95

Lys Gln His Gly Gln Phe Ser Leu Ala Val Val Ser Leu Asn Ile Thr
            100                 105                 110

Ser Leu Gly Leu Arg Ser Leu Lys Glu Ile Ser Asp Gly Asp Val Ile
            115                 120                 125

Ile Ser Gly Asn Lys Asn Leu Cys Tyr Ala Asn Thr Ile Asn Trp Lys
            130                 135                 140

Lys Leu Phe Gly Thr Ser Gly Gln Lys Thr Lys Ile Ile Ser Asn Arg
145                 150                 155                 160

Gly Glu Ala Ser Cys Lys Ala Thr Gly Gln Val Cys His Ala Leu Cys
                165                 170                 175

Ser Pro Glu Gly Cys Trp Gly Pro Glu Pro Arg Asp Cys Val Ser
            180                 185                 190

<210> SEQ ID NO 25
<211> LENGTH: 191
<212> TYPE: PRT
<213> ORGANISM: Homo sapiens

<400> SEQUENCE: 25

```
Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Thr Ser Ala Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
            85                  90                  95

Lys Gln His Gly Gln Phe Ser Leu Ala Val Val Ser Leu Asn Ile Thr
        100                 105                 110

Ser Leu Gly Leu Arg Ser Leu Lys Glu Ile Ser Asp Gly Asp Val Ile
    115                 120                 125

Ile Ser Gly Asn Lys Asn Leu Cys Tyr Ala Asn Thr Ile Asn Trp Lys
130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
            165                 170                 175

Ser Pro Glu Gly Cys Trp Gly Pro Glu Pro Arg Asp Cys Val Ser
        180                 185                 190

<210> SEQ ID NO 26
<211> LENGTH: 191
<212> TYPE: PRT
<213> ORGANISM: Homo sapiens

<400> SEQUENCE: 26

Lys Val Cys Asn Gly Ile Gly Ile Gly Glu Phe Lys Asp Ser Leu Ser
1               5                   10                  15

Ile Asn Ala Thr Asn Ile Lys His Phe Lys Asn Cys Thr Ser Ile Ser
            20                  25                  30

Gly Asp Leu His Ile Leu Pro Val Ala Phe Arg Gly Asp Ser Phe Thr
        35                  40                  45

His Thr Pro Pro Leu Asp Pro Gln Glu Leu Asp Ile Leu Lys Thr Val
    50                  55                  60

Lys Glu Ile Thr Gly Phe Leu Leu Ile Gln Ala Trp Pro Glu Asn Arg
65                  70                  75                  80

Thr Asp Leu His Ala Phe Glu Asn Leu Glu Ile Ile Arg Gly Arg Thr
            85                  90                  95

Lys Met Glu Gly Gln Phe Ser Leu Ala Val Val Ser Leu Asn Ile Thr
        100                 105                 110

Ser Leu Gly Leu Arg Ser Leu Lys Glu Ile Ser Asp Gly Asp Val Ile
    115                 120                 125

Ile Ser Gly Asn Lys Asn Leu Cys Tyr Ala Asn Thr Ile Asn Trp Lys
130                 135                 140

Lys Leu Phe Gly Thr Ser Gly Gln Lys Thr Lys Ile Ile Ser Asn Arg
145                 150                 155                 160

Gly Glu Asn Ser Cys Lys Ala Thr Gly Gln Val Cys His Ala Leu Cys
            165                 170                 175

Ser Pro Glu Gly Cys Trp Gly Pro Glu Pro Arg Asp Cys Val Ser
        180                 185                 190
```